(12) United States Patent
Cotton

(10) Patent No.: US 11,803,241 B2
(45) Date of Patent: Oct. 31, 2023

(54) WEARABLE JOINT TRACKING DEVICE WITH MUSCLE ACTIVITY AND METHODS THEREOF

(71) Applicant: Rehabilitation Institute of Chicago, Chicago, IL (US)

(72) Inventor: Ronald Cotton, Chicago, IL (US)

(73) Assignee: Rehabilitation Institute of Chicago, Chicago, IL (US)

( * ) Notice: Subject to any disclaimer, the term of this patent is extended or adjusted under 35 U.S.C. 154(b) by 447 days.

(21) Appl. No.: 16/908,337

(22) Filed: Jun. 22, 2020

(65) Prior Publication Data

US 2020/0401224 A1 Dec. 24, 2020

Related U.S. Application Data

(60) Provisional application No. 62/925,083, filed on Oct. 23, 2019, provisional application No. 62/864,916, filed on Jun. 21, 2019.

(51) Int. Cl.
*A61B 5/00* (2006.01)
*G06F 3/01* (2006.01)
(Continued)

(52) U.S. Cl.
CPC ............ *G06F 3/015* (2013.01); *A61B 5/0077* (2013.01); *A61B 5/1114* (2013.01); *A61B 5/224* (2013.01);
(Continued)

(58) Field of Classification Search
CPC ..... G06F 3/015; A61B 5/0077; A61B 5/1114; A61B 5/224; A61B 5/30; A61B 5/4528;
(Continued)

(56) References Cited

U.S. PATENT DOCUMENTS

| | | | |
|---|---|---|---|
| 7,931,604 B2* | 4/2011 | Even Zohar | G09B 23/28 |
| | | | 703/2 |
| 9,669,543 B1* | 6/2017 | Stubbs | B25J 9/1612 |

(Continued)

FOREIGN PATENT DOCUMENTS

| | | |
|---|---|---|
| WO | 2014186537 A1 | 11/2014 |
| WO | 2018033591 A2 | 2/2018 |

OTHER PUBLICATIONS

International Search Report and Written Opinion issued in corresponding Application No. PCT/US2020/038972 dated Sep. 28, 2020, 14 pages.

(Continued)

*Primary Examiner* — May A Abouelela
(74) *Attorney, Agent, or Firm* — Polsinelli PC

(57) ABSTRACT

A system for utilizing wearable, wireless-connected sensors that record both IMU and EMG muscle activity for rehabilitation with kinematic monitoring is disclosed. The system runs an efficient quaternion-based complementary filter that estimates the sensor orientation while correcting for estimate drift and constraining magnetometer estimates to only influence heading. The difference in the two sensor orientations is used to estimate the joint angle, which can be further improved with joint axis estimation. Thus, successful tracking of joint angle and muscle activity in a home environment can be accomplished with the sensors and a smartphone. Further, a system utilizing these sensors may include video-capable cameras configured for capturing a video of a pose of the user, and a game framework executable by a processor in communication with the sensors and the cameras. The system may include a game framework configured to utilize a pose trajectory and one or more joint angles determined using the sensors to provide biofeedback to a user.

19 Claims, 24 Drawing Sheets
(21 of 24 Drawing Sheet(s) Filed in Color)

(51) Int. Cl.
*A61B 5/22* (2006.01)
*A61B 5/11* (2006.01)
*A61B 5/30* (2021.01)

(52) U.S. Cl.
CPC .............. *A61B 5/30* (2021.01); *A61B 5/4528* (2013.01); *A61B 5/6802* (2013.01); *A61B 5/742* (2013.01); *A61B 2505/09* (2013.01)

(58) Field of Classification Search
CPC ... A61B 5/6802; A61B 5/742; A61B 2505/09; A61B 5/0022; A61B 2560/0214; A61B 2562/0219; A61B 5/1122; A61B 5/1123; A61B 5/1127; A61B 5/257; A61B 5/313; A61B 5/6824; A61B 2562/164; A61B 5/1495; A61B 5/458; A61B 5/7225
See application file for complete search history.

(56) References Cited

U.S. PATENT DOCUMENTS

| | | | | |
|---|---|---|---|---|
| 10,271,773 | B2* | 4/2019 | Chang | G06F 3/011 |
| 10,276,020 | B2* | 4/2019 | Chang | A61B 5/1116 |
| 10,314,520 | B2* | 6/2019 | Hauenstein | G01C 21/183 |
| 10,716,517 | B1* | 7/2020 | McNair | A61B 5/742 |
| 2015/0148708 | A1 | 5/2015 | Cordo | |
| 2016/0058519 | A1* | 3/2016 | Herr | A61F 2/5044 600/587 |
| 2017/0259428 | A1* | 9/2017 | Assad | G16H 40/67 |
| 2017/0273601 | A1 | 9/2017 | Wang et al. | |
| 2018/0116897 | A1 | 5/2018 | Lee et al. | |
| 2018/0338720 | A1* | 11/2018 | Gupta | G06F 1/163 |
| 2019/0167988 | A1 | 6/2019 | Shahriari et al. | |
| 2019/0274911 | A1* | 9/2019 | Kesner | A61F 2/583 |
| 2019/0313966 | A1* | 10/2019 | Lanzkowsky | A61B 5/165 |
| 2019/0343662 | A1* | 11/2019 | Song | A61F 2/586 |
| 2019/0385476 | A1* | 12/2019 | Sadeghi | G09B 19/0038 |
| 2020/0061378 | A1* | 2/2020 | Ganguly | A61B 5/4824 |
| 2020/0367823 | A1* | 11/2020 | Chahine | A41B 11/00 |
| 2021/0138240 | A1* | 5/2021 | Tomita | A61B 5/7455 |
| 2021/0162262 | A1* | 6/2021 | Lee | A63B 23/0494 |
| 2021/0236020 | A1* | 8/2021 | Matijevich | A61B 5/7455 |
| 2021/0283001 | A1* | 9/2021 | Von Zitzewitz | A61B 5/7282 |

OTHER PUBLICATIONS

Partial Supplementary European Search Report issued in related Application No. 20826786.4 dated May 2, 2023, 14 pages.
Cotton et al., Wearable Monitoring of Joint Angle and Muscle Activity, 2016 IEEE 16th International Conference on Rehabilitation Robotics (ICORR), IEEE, Jun. 24, 2019, pp. 258-263. 2019.
Giuffrida et al., Upper-Extremity Stroke Therapy Task Discrimination Using Motion Sensors ad Electromyography, IEEE Transactions on Neural Systems and Rehabilitation Engineering, IEEE, USA, vol. 16, No. 1, Feb. 1, 2008, pp. 82-90. 2008.
Schauer, Sensing motion and muscle activity for feedback control of functional electrical stimulation: Ten years of experience in Berlin, Annual Reviews in Control, vol. 44, pp. 355-374. 2017.
European Patent Office, Communication Pursuant to Article 94(3) EPC, Applicaton No. 20826786.4, dated Sep. 6, 2023, 13 pages.
Tannous, H et al., "A New Multi-Sensor Fusion Scheme to Improve the Accuracy of Knee Flexion Kinematics for Functional Rehabilitation Movements," Sensors, vol. 16, No. 11, Nov. 15, 2016, pp. 1-17.
Zhang, Z., "Cameras and Inertial/Magnetic Sensor Units Alignment Calibration", IEEE Transactions on Instrumentation and Measurement, IEEE, USA, vol. 65, No. 6, Jun. 1, 2016, pp. 1495-1502.

* cited by examiner

WEARABLE JOINT TRACKING DEVICE WITH MUSCLE ACTIVITY AND METHODS THEREOF

CROSS REFERENCE TO RELATED APPLICATIONS

This is a U.S. non-provisional patent application that claims benefit to U.S. provisional patent application Ser. No. 62/864,916 filed on Jun. 21, 2019, and to U.S. provisional patent application Ser. No. 62/925,083 filed on Oct. 23, 2019; all of which is herein incorporated by reference in its entirety.

FIELD

The present disclosure generally relates to systems and methods for neurological rehabilitation; and in particular, to a device and associated methods for wearable joint tracking with muscle activity.

BACKGROUND

In a rehabilitation setting, analysis of muscle activity and movement or motion is key to assessing any progress of a patient. The gold standard to measure movement generally is marker-based optical motion capture, limiting it to a laboratory setting. While wireless EMG systems are more portable, the majority of these require at least a nearby computer to record. A promising and increasingly popular approach to motion tracking that can step outside the laboratory uses inertial measurement units (IMUs) to track the relative movement of body segments. However, these sensors record rotation, linear acceleration and magnetic flux rather than body position and orientation, and inferring these is a challenging technical problem.

It is with these observations in mind, among others, that various aspects of the present disclosure were conceived and developed.

BRIEF DESCRIPTION OF THE DRAWINGS

The present patent or application file contains at least one drawing executed in color. Copies of this patent or patent application publication with color drawing(s) will be provided by the Office upon request and payment of the necessary fee.

FIGS. 5a and 5b show the absolute orientation of the two sensors. FIG. 5c shows the rotation magnitude between two attitudes. FIG. 5d shows axis of rotation, relative to the first sensor. FIG. 5e shows the rotation angle projected along the dominant rotation axis.

FIG. 6c shows the estimated elbow angle. FIG. 6d shows the raw gyroscope measurements in the sensor frame and the rotation around the estimated elbow axis. FIG. 6e shows EMG activity measured over the bicep muscle.

FIG. 8c shows the estimated knee angle. FIG. 8d shows quadriceps EMG activity.

Corresponding reference characters indicate corresponding elements among the view of the drawings. The headings used in the figures do not limit the scope of the claims.

DETAILED DESCRIPTION

Summary

Figure 1A:
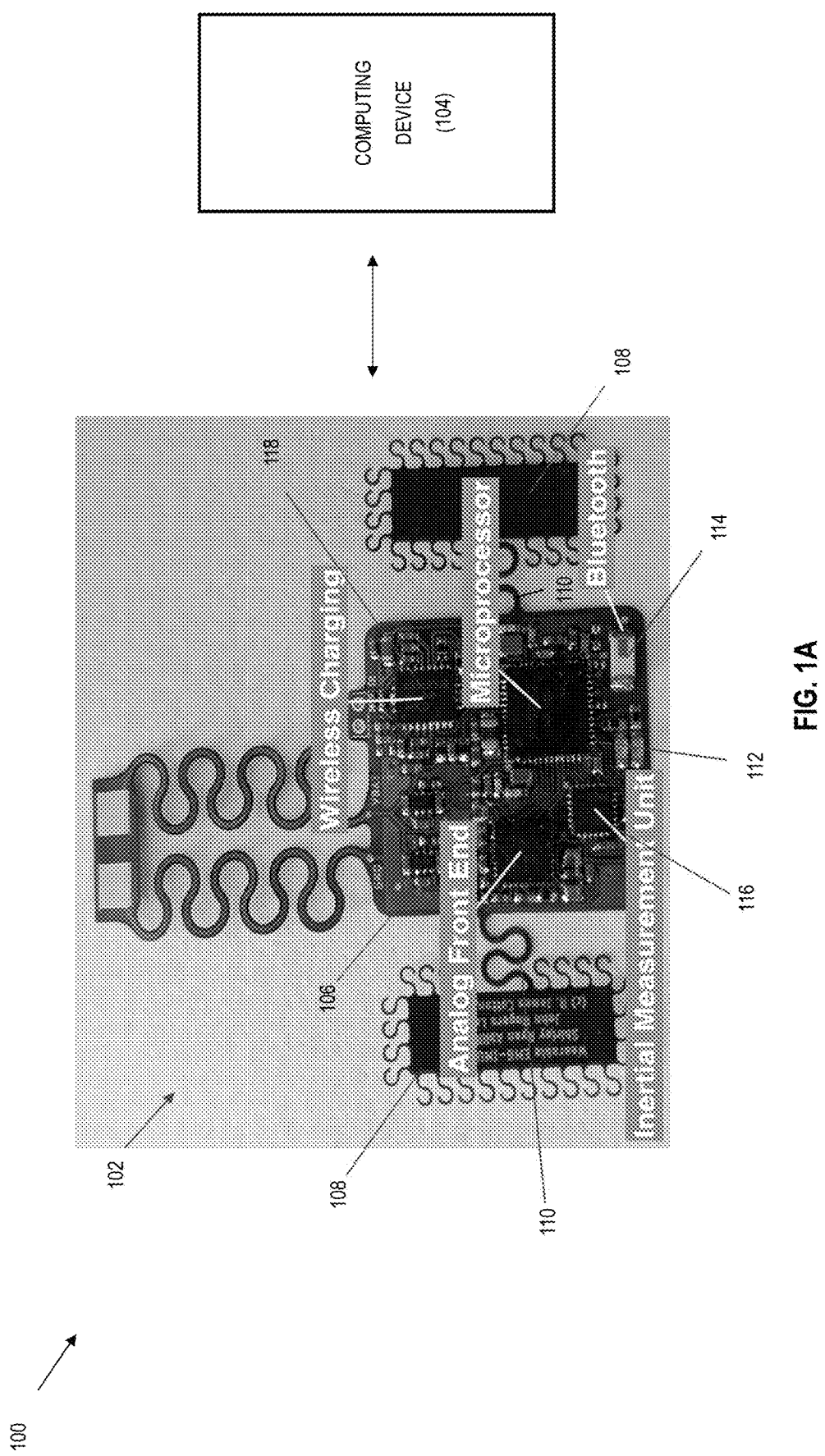
FIG. 1A is a photograph showing one embodiment of a system including a wearable sensor of the instant disclosure.

In the present application, a system including at least one wearable device is described that allows simultaneous joint angle and EMG tracking with data acquired by a Bluetooth connected smartphone that allows continuous monitoring outside the laboratory setting. This may be comprised of several components: 1) the flexible, wearable EMG and IMU sensor, firmware, and smartphone software; 2) an efficient onboard pose estimation algorithm, which are combined to estimate joint angle; and 3) an algorithm to compute joint angles from the poses from multiple sensors. In one embodiment, the pose estimation algorithm is a complementary filter that improves accuracy by tracking the gyroscope bias and constraining updates from the magnetometer to only influence the heading. This system may be deployed to successfully track both elbow angle with biceps brachii activity and knee angle with quadricep activity in a home environment, which can be used either with sensors alone or optionally, in conjunction with one or more video cameras for additional refinement. In some embodiments, the present system allows tracking of more complicated joints such as the shoulder and hip. The present system breaks the constraints of conventional solutions and allows simultaneous joint and muscle activity recording free of the laboratory.

Further embodiments of the system include at least one wearable device where the system provides calibration thereof; and pose trajectory determination is also described herein. In these embodiments, the system includes a stereo video setup comprising at least one video camera and a processor. In some embodiments, the system fuses the data from the stereo video setup and the wearable device to model biomechanically plausible pose trajectory. Joint locations are first extracted from a video captured by the stereo video system and initial pose estimates are determined for each frame of the video. The pose trajectory as determined from the video is then optimized using a plurality of smoothing techniques through application of several loss functions and application of biomechanical constraints. With these calibrations, pose estimation can then be performed using data from the wearable devices alone. The system can be implemented to provide biofeedback in the form of therapy games.

In general, the system detects muscle movements in real time for rehabilitation purposes. The system estimates the orientation (pose) of a single sensor (which also includes mag calibration), estimates joint axis with sensors for joints with one degree of freedom (such as the elbow or the knee), and in some embodiments can calibrate an orientation and position of the sensors relative to the body for more improved accuracy in tracking using video calibration. Video calibration can allow more accurate tracking afterwards with just the sensors being worn, and the user need not use the cameras to track movement. These functionalities allow the system to detect meaningful movements in real time that is detected on the smartphone and can be used for rehabilitation. In some embodiments, these tools can be applied to provide therapy and biofeedback in the form of interactive games.

In addition, purposes using this system include both outcome and performance monitoring as well as therapeutic. Outcome and performance include collecting data of muscle activity and movement patterns throughout recovery and in the home environment. Therapeutic uses include guiding self-dosed therapies through biofeedback games. (The foregoing being elaborated herein).

Introduction and Technical Challenges:

The present novel concept incorporates simultaneous measurement of joint angle and muscle electromyography (EMG) which is believed to be of significant clinical and research interest. In the rehabilitation setting, such combined recording can provide objective outcome scores, characterize pathological biomechanics such as spasticity, and longitudinally monitor recovery. IMUs can be used to track relative movement of body segments, and can record rotation, linear acceleration and magnetic flux rather than body position and orientation. However, inferring these properties is a challenging problem. Many approaches can be decomposed first into estimating the pose (i.e. attitude or orientation) of an individual sensor (and thus ideally a body segment) and then combing this information to track joint angles.

Pose estimation from inertial sensor data has a strong history from the aeronautical field, and one popular class of algorithms is the complementary filter. Complementary filters integrate rotation (from the gyroscopes) to obtain a good high-frequency response and then correct this estimate with the accelerometer and magnetometer to rejected drift and obtain a good low-frequency response. These methods depend on good sensor calibration, but can still be biased, for example, by external sources of magnetic field disturbances. Some approaches to reduce this error include tracking changes in the gyroscope biases and constraining the magnetometer to only influence the heading.

There are also a number of ways to combine sensors to infer the joint angle. For example, some do not require the heading estimate, but rather integrate the gyroscopes directly along the inferred axis of the joint with accelerometers providing drift reduction. Alternatively, by using the full 3D pose, the angle of a joint can then be measured as the difference in pose of two body segments. These estimates can be improved by adding anthropomorphic measurements and biomechanical constraints, for example, including that the knee joint is a single-axis hinge joint.

3D pose estimation algorithms can include very flexible non-limiting models, such as the Skinned Multi-Person Linear (SMPL) model. However, these exceed the anatomic degrees of freedom at many joints, which prohibits a unique mapping from the pose parameters to interpretable joint angles. It is also important to note that the datasets used to train all these algorithms are from able-bodied populations, and have not been widely tested on the rehabilitation population where patients might have movement impairments (e.g. dystonia or hemiplegia), be using an assistive device (e.g. walker or wheelchair) or have other anatomic variations (e.g. amputations) not seen in the training datasets.

Wearable sensors with inertial measurements units (IMUs) also offer great promise for highly available kinematic monitoring with the benefit of being able to track movement when video is unavailable. Mapping the inertial data from multiple sensors into biomechanical movement first requires fusing data from a single sensor into an estimate of attitude and then combining the data from multiple sensors to extract either biomechanical movement or a full 3D pose. A particular challenge is that sensors can be positioned arbitrarily on body segments, which limits mapping sensor movements to body movements without a careful calibration routine. However, this can be addressed by fusing IMU data with video-based pose estimation to compute the relative alignment of the sensor on a body segment, as will be discussed in further detail below. It should be noted that once the alignment has been determined using the video-based pose estimation, the data from the sensors can be used without aid from the camera. This allows the system 100 to have a better understanding of the user's movements.

Figure 1B:
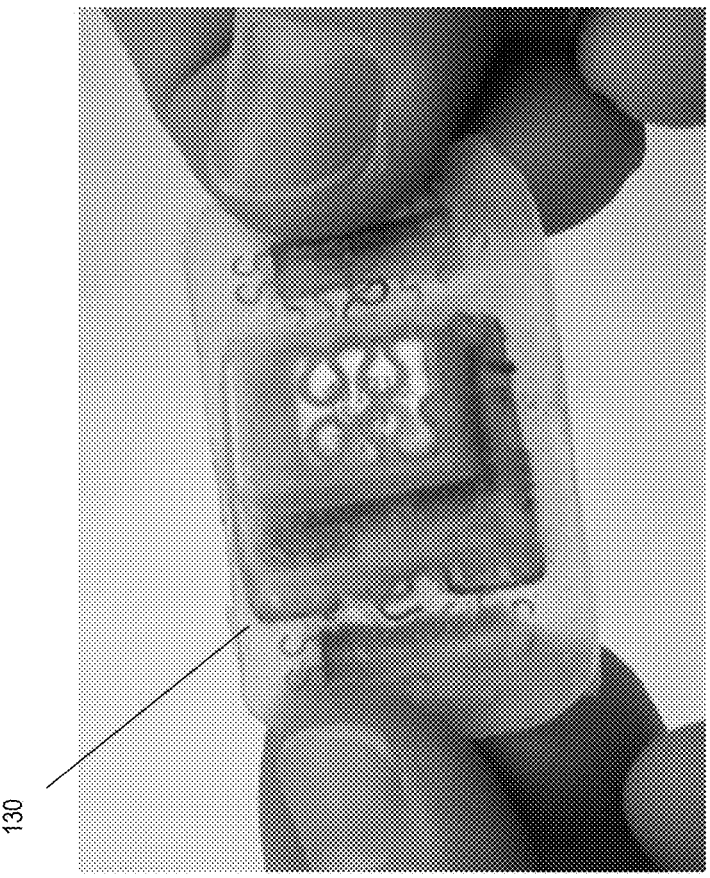
FIG. 1B is a photograph that shows the sensor of FIG. 1A after encapsulation.

Embodiments of the System:

Referring to FIG. 1A, a system 100 is shown for wearable joint tracking with muscle activity. Leveraging recent advances in flexible and stretchable electronics, the system includes at least one comfortable wearable electromyography sensor 102, referred to herein as sensor 102 or sensors 102, in operable communication with a computing device 104, such as a mobile device or smartphone. The design of the sensor 102 may be fabricated using a 0.1 mm thick flexible circuit board 106; the circuit board 106 providing a base or substrate for the sensor 102 as shown. Electrodes 108 of the sensor 102, configured for accessing EMG data, may be in operable communication with the circuit board 106 of the sensor 102 via serpentine wires 110 (with individual bodies of the electrodes 108 being separated from the circuit board 106), making the sensor 102 robust to twisting, stretching and rotation. The components of the sensor 102 may further be embedded or encapsulated within an encapsulating layer (130 in FIG. 1B), e.g., which may include a bottom layer of silicone with the rest of the circuitry floating above it. The EMG signals of the sensor 102 may be amplified and bandpass filtered before being digitized by a microprocessor 112 (e.g., by non-limiting example, nRF52832, Nordic Semiconductor, Norway). The sensor 102 may also include a wireless chip 114 or other such electrical component for wireless connectivity and communication capabilities, such as Bluetooth®, and the microprocessor 112 may also handle the Bluetooth connectivity and/or other wireless technologies. As further indicated in FIG. 1A, the sensor 102 may also include at least one inertial measurement unit (IMU) 116, and wireless charging 118. It should be understood and appreciated that the design of the sensor 102 may take on various forms and include different components. In other words, the embodiments of the sensor 102 described herein are merely non-limiting examples and different sensor embodiments are contemplated without departing from the scope of the novel disclosure.

Firmware of the sensor 102 digitizes the EMG data from the electrodes 108 at a specified sampling frequency and applies additional digital bandpass filtering. In some embodiments, the selected sampling frequency is 2 KHz, however the system 100 is not limited to this frequency and can in some embodiments be sampled at a faster rate. The waveform length algorithm is used to extract EMG activity from subsequent 20 millisecond windows. The firmware exposes this data under an EMG Bluetooth Service as both the raw digitized EMG and the EMG power via corresponding Bluetooth characteristics. The Bluetooth standard limits the frequency a characteristic can be updated, so multiple raw samples are packaged into a single characteristic update to allow streaming the full 2 KHz bandwidth. A single EMG activity sample is stored per characteristic to minimize the latency for real time feedback.

The circuit of the sensor 102 also contains the IMU 116, which may be a 9-axis inertial measurement sensor, which records the acceleration, rotation and magnetic data (e.g., MPU-9250, Invensense, San Jose, US). In one embodiment, the IMU 116 was sampled at 500 Hz with the maximum rotation rate set to 500°/s and maximum acceleration of 16G. Note that these parameters are not limited to the given values, but are given for illustration purposes. This data is captured by the microprocessor 112 and used to generate the pose estimate (algorithm described below). An IMU Bluetooth service may be leveraged to organize this data, which includes a characteristic for the accelerometer, gyroscope and magnetometer, respectively. Again, multiple samples are bundled into each characteristic to facilitate streaming. A single pose estimate is stored in a separate characteristic for every three raw data samples.

The system 100 may further include an accompanying software suite, or smartphone application for mobile applications, executable by the computing device 104 or otherwise. This includes a core service that handles the Bluetooth connectivity to fetch the inertial and EMG activity from the sensor 102. User applications allow monitoring this activity and obtaining biofeedback in the form of games. Data from smartphone applications executable by the computing device 104 may be securely transferred to Google Firestore or other such cloud service for monitoring and analysis. Data presented in this disclosure may be acquired via this system 100 from a home environment and the data fetched from the cloud for analysis.

The smartphone application (e.g. 511 in FIG. 23; and also illustrated in FIGS. 17-18 as executed by a smartphone) can optimize the Bluetooth bandwidth by only subscribing to the desired characteristics, for example, by choosing between either raw IMU data or the internal pose estimate or by selecting either the raw EMG stream versus the onboard power extraction. To optimize power consumption, the amplifiers and IMU are placed into a low power mode when there is no subscriber to the corresponding data.

Figure 2:
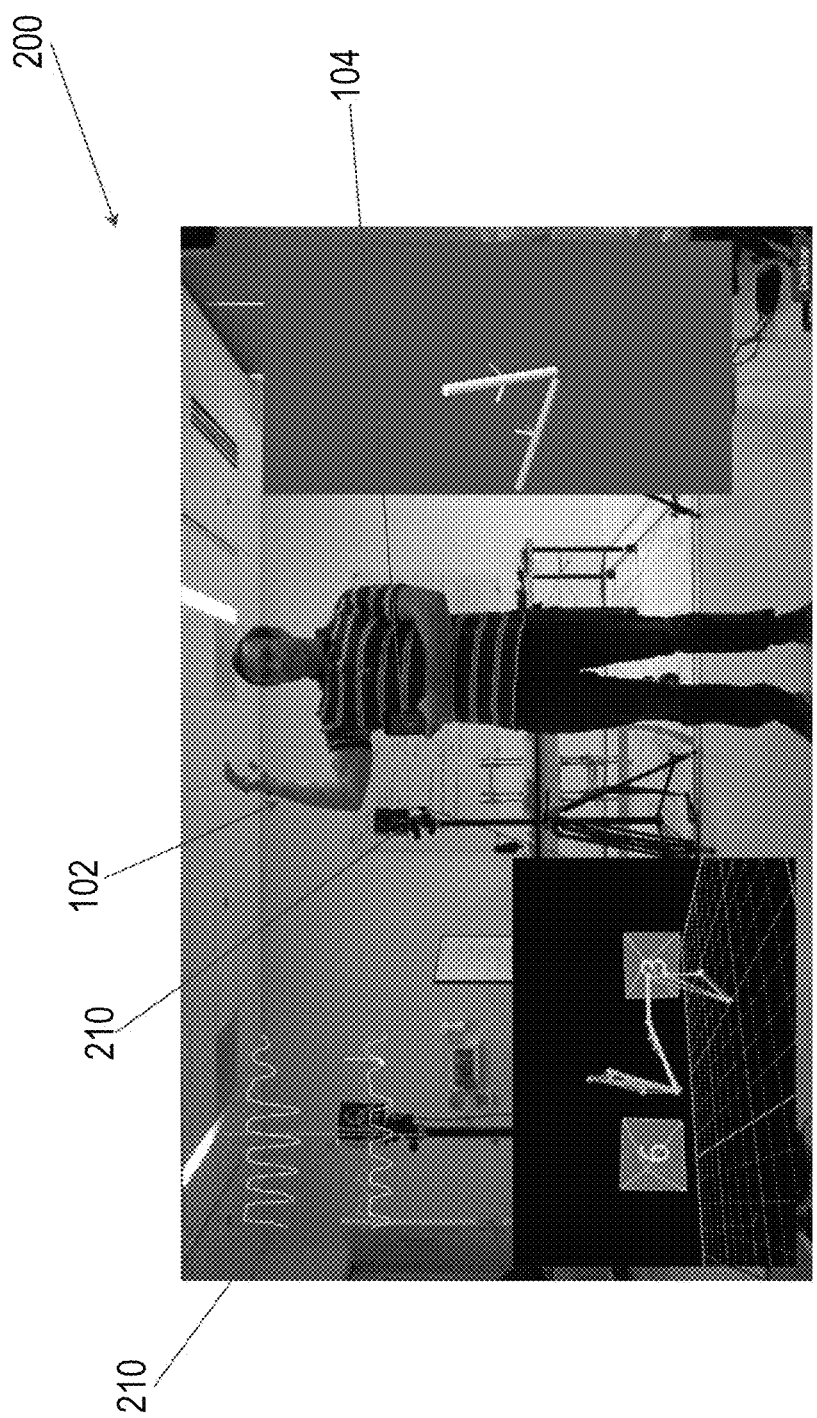
FIG. 2 is a photograph that shows a tracking platform which utilizes the wearable sensor of FIGS. 1A and 1B and incorporates a dual-camera setup for joint angle determination and calibration of the wearable sensor.

Referring to FIG. 2, the system 100 may include or otherwise relate to a tracking platform 200 for calibrating the wearable sensor 102 and tracking joint movement. The tracking platform 200 includes one or more video cameras 210 in communication with a processor 220. In some embodiments, the tracking platform 200 and the wearable sensor system 100 may both be in communication with the computing device 104. A user can wear the wearable electromyography sensor 102 and stand in front of the video cameras 210 to jointly produce temporally smooth and biomechanically realistic pose estimates and joint angles. Further, the tracking platform 200 can be used to calibrate the wearable sensor system 100 to accurately estimate joint angles. Data collected using the system 100 and/or platform 200 can be used to provide biofeedback in the form of a therapy game, playable on a computing device such as the computing device 104.

Calibration

Figure 3:
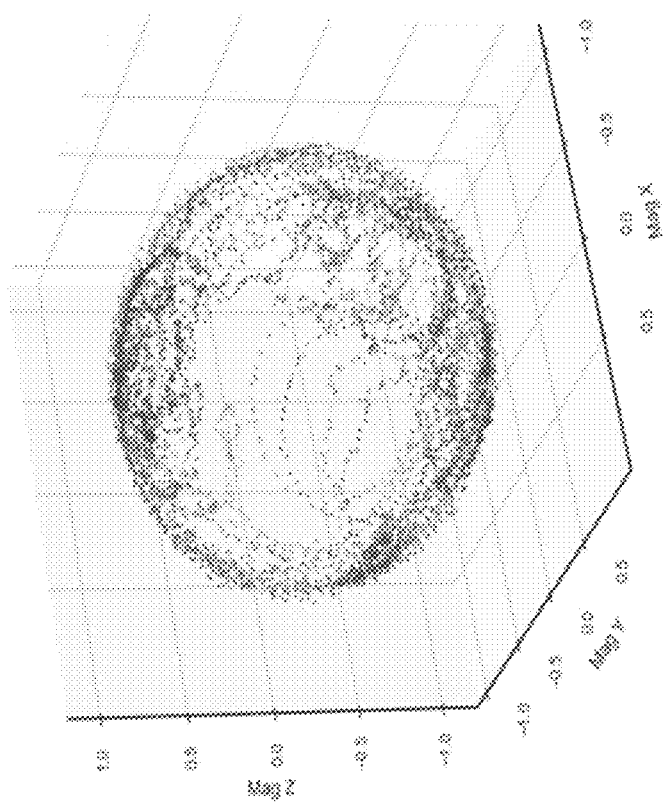
FIG. 3 is an image that depicts samples from two magnetometers during calibration after removal of the bias, demonstrating spherical shapes centered at origin.

To obtain a good pose estimate including the heading, it is important to perform an accurate calibration of the magnetometer. This may be achieved by rotating the sensor 102 to fully cover all of these possible orientations and then transforming it into a sphere. Numerous methods would be appreciated by those skilled in the art including ellipsoid fitting to account for hard and soft iron distortions. For demonstration, this was performed offline for each instance of the sensor 102 and then transferred to the sensor 102 where it is stored in the flash settings. FIG. 3 shows samples from the magnetometer of two examples of the sensor 102 (i.e., two sensors) while rotating, demonstrating a spherical distribution after calibration.

In some embodiments and as will be discussed in greater detail below, the sensor 102 can be calibrated using the system 200 to compute a relative alignment of the sensor 102 on a body segment.

The cameras themselves can be calibrated using a checkerboard pattern that could be seen by both cameras 210 and was used to estimate both the intrinsic and extrinsic camera parameters with relative rotation and offset. This parameterizes a simple pinhole camera model that predicts how coordinates in 3D space map onto 2D image space.

Attitude Estimation

An efficient quaternion-based attitude estimation algorithm was designed that can be implemented in real-time on the wearable sensor/s 102. For the purposes of this application, it is sufficient to know the quaternions are a four-element vector representation of orientation with unit length that be easily converted back into Euler angles (roll, pitch and yaw). They have the benefit of being compact, efficient to work with, and not suffering from gimbal lock.

Complementary filters may be used to compute pose estimate from 9-axis inertial data. They work by integrating the gyroscope measurements to obtain a good high frequency response and use the accelerometer and magnetometer for improved slow frequency response by correcting for gyroscope drift. Here, an efficient quaternion-based complementary filter is extended to provide more robust attitude estimates across the variety of poses a person may take. The axis convention for this filter uses the NED (North-East-Down) convention common in aeronautical systems. Measurements will be described as either in the world reference frame or the sensor reference frame.

Let $\omega$ be the vector of rotation rates (in rad/s) along each axis, measured by the gyroscope, and q be the quaternion representation of the current pose. The gyroscopes also have a bias ($\omega_b$) that changes over time, which the filter should track as well. If the gyroscope's measurements and bias were perfect, the state could be propagated forward in time from these measurements using the matrix that transforms from angular rates to a change in the quaternion state and then integrating this dynamical system.

$$\Omega(q) = \begin{bmatrix} -q1 & -q2 & -q3 \\ q0 & -q3 & q2 \\ q3 & q0 & -q1 \\ -q2 & q1 & q0 \end{bmatrix} \quad (1)$$

$$\dot{q} = \frac{1}{2}\Omega(q)(\omega - \omega_b)$$

However, inevitable errors in the gyroscope measurements and changes in bias will be accumulated, resulting in a drift in the attitude estimate. This drift can be corrected with the accelerometer and magnetometer readings, which provide a reference to the world frame.

In a stationary frame, the accelerometer should only measure gravity, which is a good first approximation for participants not moving significantly. Thus, any misalignment between the accelerometer axis and the predicted gravity (down) axis is an error. The rotation to correct that error can be computed by taking the cross product between the measured and predicted acceleration. To compute the predicted acceleration, $R_{be}$ is used which rotates a vector from the world frame into the sensor (body) frame. Let a be acceleration measured along each axis in the sensor reference frame and g point in the upward direction.

$$R_0 = [q_0^2 + q_1^2 - q_2^2 - q_3^2 \; 2(q_1q_2 + q_0q_3) \; 2(q_1q_3 - q_0q_2)]$$

$$R_1 = [2(q_1q_2 - q_0q_3) \; q_0^2 - q_1^2 + q_2^2 - q_3^2 \; 2(q_2q_3 + q_0q_1)]$$

$$R_2 = [2(q_1q_3 + q_0q_2) \; 2(q_2q_3 - q_0q_1) \; q_0^2 - q_1^2 - q_2^2 + q_3^3]$$

$$R_{be}(q) = [R_0^T \; R_1^T \; R2^T]^T \quad (2)$$

$$e_a = \frac{a}{\|a\|} \times R_{be}g \quad (3)$$

The accelerometer correction does not give any feedback to the heading estimate, but heading can be disambiguated with the magnetometer. However, magnetometers are more susceptible to distortions than gravity so it is desired to constrain this update to only influence heading; $\psi$. This is done by projecting the analogous correction from the magnetometer onto the derivative of the quaternion state with respect to a change in heading, $$\frac{\delta q}{\delta \psi}.$$

It is also important to compute the predicted magnetic flux ($B_e$) for a given location using the world magnetic model. Let m be a vector containing the magnetic flux measured along each axis.

$$e_m = \frac{m}{\|m\|} \times R_{be}B_e$$

$$\frac{\delta q}{\delta \psi} = [-q_3 \; -q_2 \; q_1 \; q_0]^T$$

$$\dot{q}_m = \left(\frac{\delta q}{\delta \psi} \cdot \frac{1}{2}\Omega(q)e_m\right)\frac{\delta q}{\delta \psi}$$

The updates from the gyroscope, accelerometer and magnetometer can then be combined to create a robust pose estimate:

$$\dot{q} = \frac{1}{2}\Omega(q)(\omega - \omega_b + K_{pa}e_a) + K_{pm}\dot{q}_m \quad (4)$$

$$\hat{q}_{t+1} = q_t + \dot{q}\Delta t \quad (5)$$

It is also helpful to track changes in the gyroscope bias as this can change with time and temperature. Both $e_a$ and $e_m$ are the rotational errors in the body frame which makes them easy to feed back. However, again it is important to constrain the magnetometer changes to only the heading axis (which depending on the sensor orientation can map to any axis in the sensor frame). This can be done using the transpose of $\Omega(q)$.

$$\omega_{b,t+1} = \omega_{b,t} - K_{ia}e_a - K_{im}\Omega(q)^T\dot{q}_m \quad (6)$$

Figure 4:
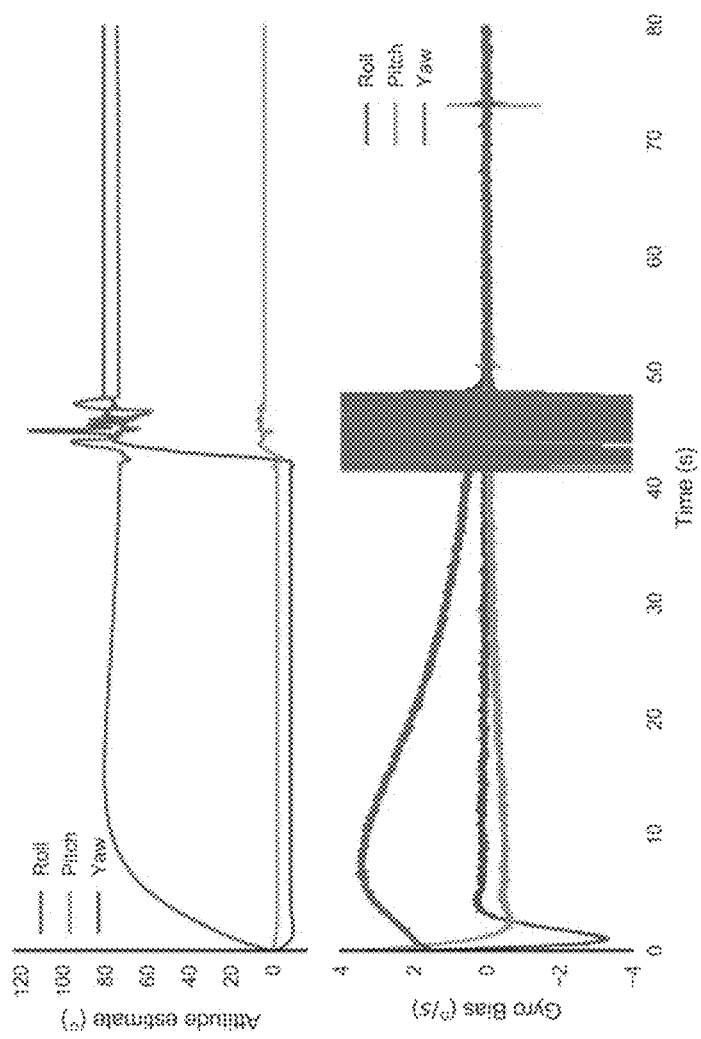
FIG. 4 is set of images that depicts gyro bias tracking and attitude convergence from a poor initialization. The sensor was enabled and left flat for 40 seconds and then rotated to vertical. The top panel shows the online attitude estimate converging to the correct values then stabilizing. The bottom panel shows the gyroscope measurements after bias correction demonstrating them being corrected to zero bias. For the initial segment when the sensor is flat only the magnetometer measurements influence the yaw bias, hence the different time scale.

This pose filter was implemented in C to run on the microprocessor 112. Having an online implementation is critical when using Bluetooth as otherwise gaps or dropped data can make offline reconstruction challenging. FIG. 4 shows the pose estimate and gyro calibration in two positions, with the attitude holding steady in each after convergence. The bias corrected gyro measurements correctly track to zero, showing a slightly different time course for different axes due to a differing values of $K_{ia}$ and $K_{im}$.

Joint Angle Estimation

For joint angle estimation, the present system 100 does not always require video data but can analyze data from the sensors 102 to estimate joint angle of a user. It should be noted that the present system 100 in absence of the video data is intended for joints which move about a single axis (i.e. knee and elbow joints).

Each sensor 102 produces a quaternion pose estimate and visualizing these directly is not an intuitive way to understand their relative orientations. Calculating the relative rotation between two quaternions, however, is fairly straightforward. The quaternion inverse $q^{-1}$ is an operator that reverses a rotation. If the poses from two sensors are r and s, then $q=r^{-1}s$ is the 3-dimensional rotation from the former to the later. This can be further decomposed into the rotational angle (θ) and the axis (v) of that rotation.

While this is mathematically correct, in practice it will not give the desired angle. This is because the sensors can be positioned on the limbs arbitrarily and this rotation must be accounted for. This can be resolved by measuring the pose of each sensor 102 with the joint at neutral and removing this baseline orientation from subsequent measurement, thus in effect mathematically aligning the two sensors in this position. Next, the angle between these corrected orientations ($\hat{r}$ and $\hat{s}$) is estimated as shown below.

$$\theta(q) = \arctan\left(\sqrt{q_1^2 + q_2^2 + q_3^2}, |q_0|\right) \qquad (7)$$

$$v(q) = \frac{1}{\sqrt{1-q_0^2}} \begin{bmatrix} q_1 \\ q_2 \\ q_3 \end{bmatrix} \qquad (8)$$

$$\hat{r}_t = r_0^{-1} r_t, \hat{s}_t = s_0^{-1} s_t$$

$$\theta_{r \to s} = \theta(\hat{r}_t^{-1} \hat{s}_t) \qquad (9)$$

Figure 5:
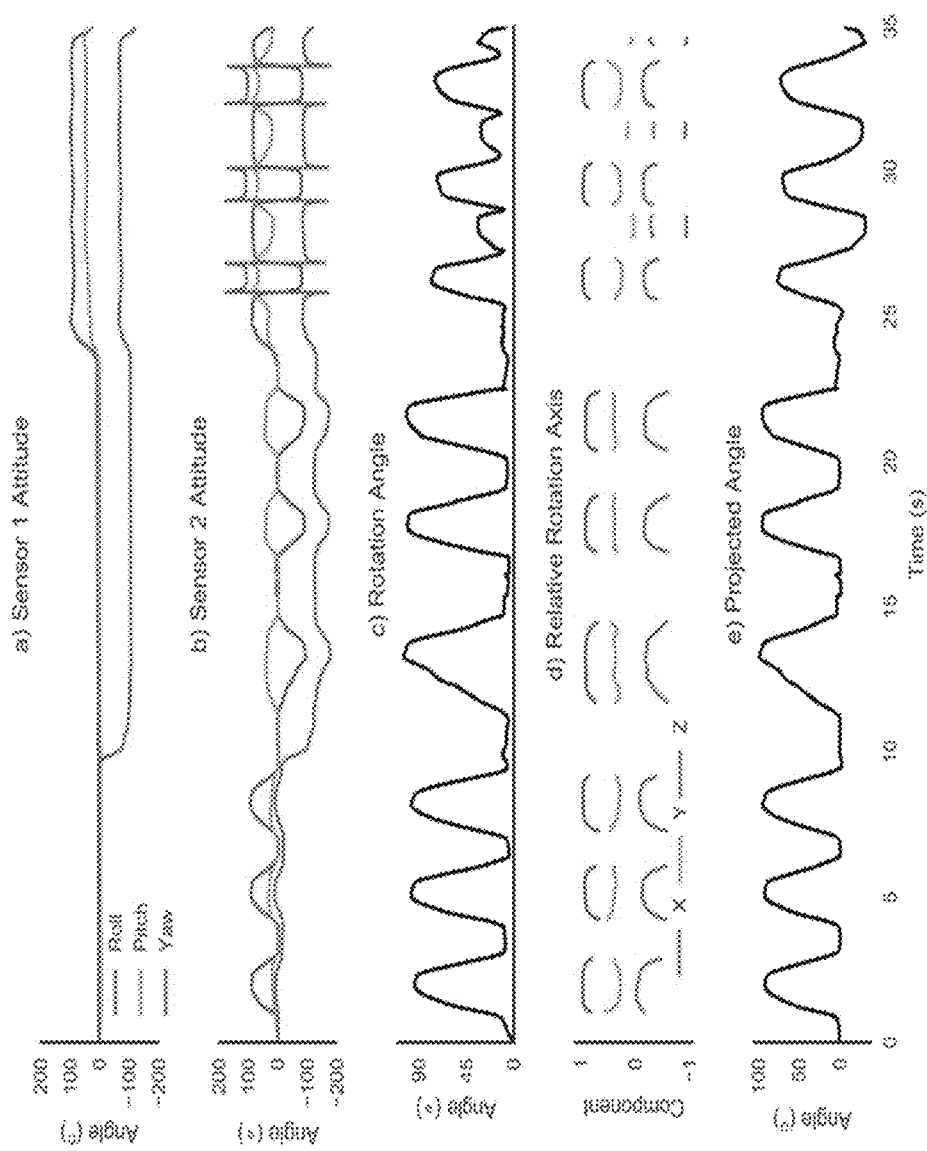
FIG. 5 is a set of images that demonstrates the algorithm with two sensors mounted across a rigid hinge rotating around three different directions.
Figure 6:
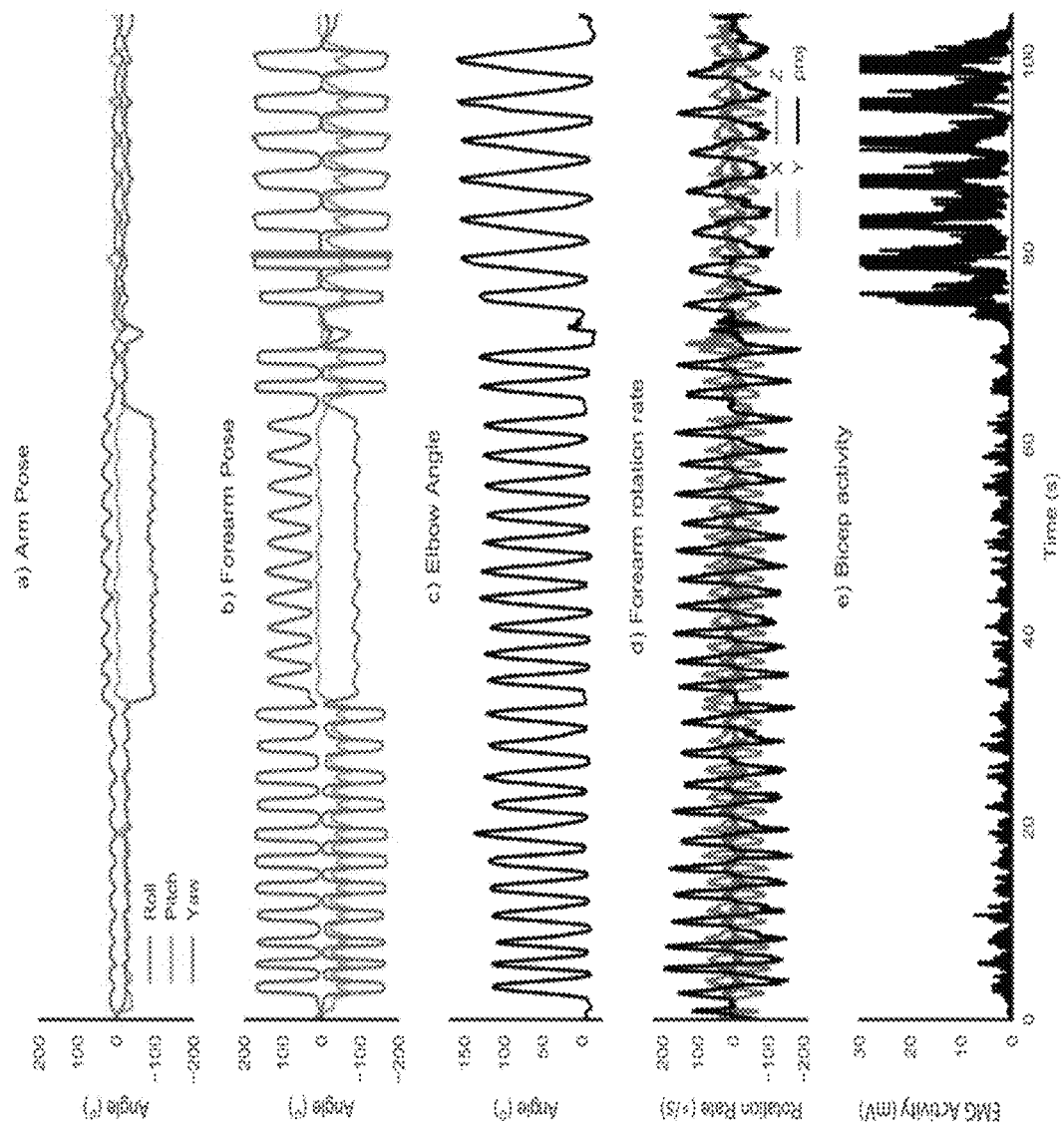
FIG. 6 is a set of images that depicts bicep activity and elbow angle during curls. The absolute orientation of a sensor placed on a) the bicep (FIG. 6a) and the forearm (FIG. 6b).
Figure 7:
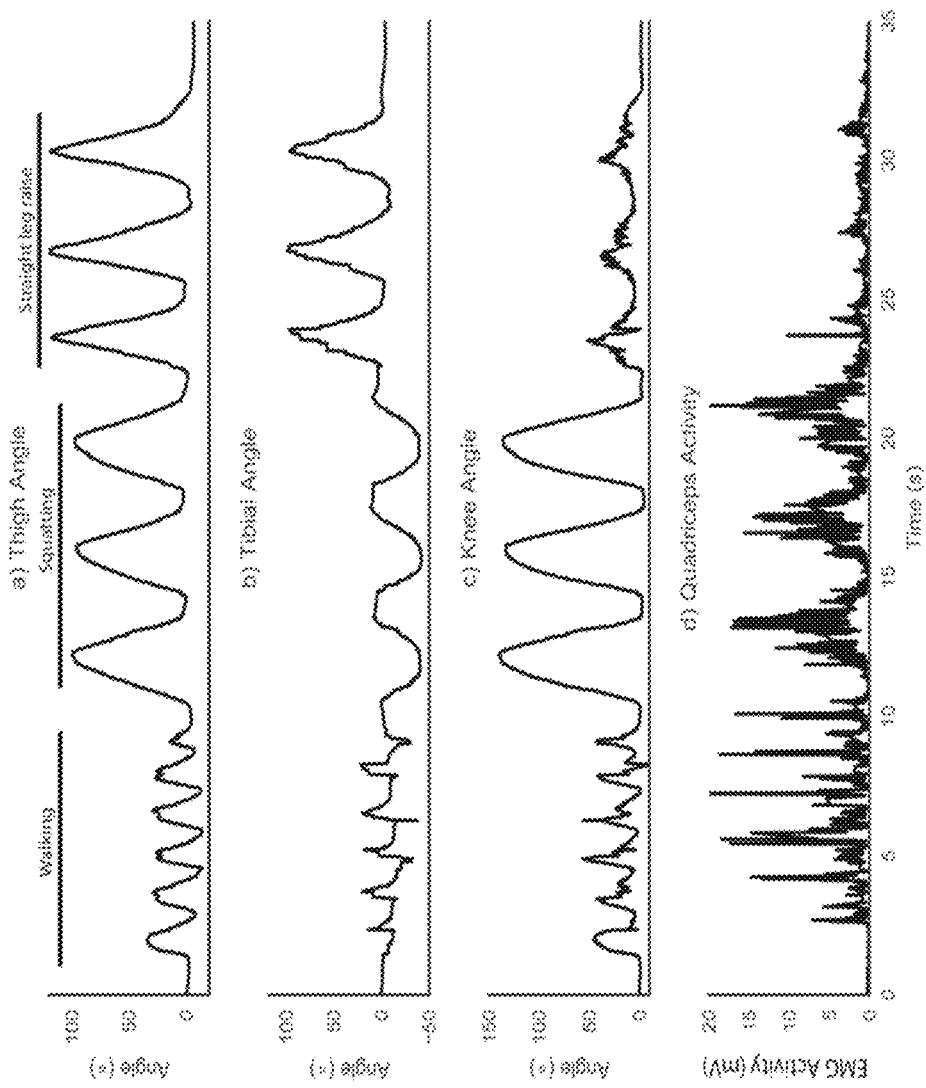
FIG. 7 is a set of images that depicts knee activity tracking during walking, squatting and leg raise. Rotation of a sensor placed on a) the thigh (FIG. 8a) and b) the tibia (FIG. 8b).

FIG. 5 (which includes FIGS. 5A-5E) demonstrates this algorithm with two sensors mounted on a rigid hinge. Sensor 2 was rotated ninety degrees relative to sensor 1 multiple times, and then the orientation of the entire hinge was changed. As desired, the estimated rotation angle continues to capture the real angle. The axis of rotation between the two sensors can be measured with Equation 8 (above) and is shown in FIG. 5D of FIG. 5, showing this is constant despite the whole system rotating, which a hinge physically enforces.

This constant axis constraint of a hinge joint is true for many joints in the body, although of course the shoulder and hips are multi-axial and even the elbow admits some supination and pronation. It can be exploited by estimating this axis relative to one of the sensors and then estimating the joint angle as rotation only around this axis. This can be done easily with a different representation of orientation called a rotation vector (Equation 10), which uses a three-element representation that folds the unit norm of a quaternion into it. This has the benefit of keeping many properties of rotation Cartesian. Because of this, principal component analysis can be used and rotation vector can be projected only along the first principal component, v, which also represents the axis of rotation as a unit norm vector. The rotation angle around v is the length of this projection (in radians).

$$r = [q_1 \ q_2 \ q_3]^T \frac{1}{\sqrt{1-q_0}} \qquad (10)$$

$$\theta = r \cdot v \qquad (11)$$

The benefits of this additional step for data visualization can be seen in the last panel of FIG. 5E of FIG. 5. In the last three movements when the hinge was oriented vertically it was extended past the zero reference. In this case, the angle estimated with Equation 9 shows a double bump since it does not preserve the sign but Equation 11 does. This step also makes the analysis slightly less sensitive to calibrating the zero pose. If rotation around two axes is desired, such as to measure supination at the elbow, more sophisticated methods can be used such as in P. Muller et al., "Alignment-Free, Self-Calibrating Elbow Angles Measurement Using Inertial Sensors," IEEE Journal of Biomedical and Health Informatics, Vol. 21, No. 2, pp. 312-319, March 2017.

Finally, with the joint axis identified, rotation rate around this axis can be measured directly by transforming the gyroscope measurements. The difference between these transformed rotations between each sensor 102 should be the same as the derivative of the estimated joint angle estimated above. This provides a nice consistency check, and also can be more accurate for the higher frequency structure such as if the rotational velocity is explicitly desired. This is performed with the same inverse rotation that generated the neutral pose above applied to the gyroscope measurements, and then projecting the rotated rotation rates along v.

$$\frac{\delta \theta}{\delta t} = R_{be}(r_0^{-1}) \omega \cdot v \qquad (12)$$

Smartphone Application for Real-Time Visualization

Data from the complementary filter running onboard the wearable sensors 102 is transferred via Bluetooth to the accompanying android or other mobile application. This allows extracting and visualizing the joint angle(s) in real-time from multiple sensors 102. The sensors 102 also send the electromyographic data in parallel, allowing the simultaneous monitoring of both. Data is also streamed to the cloud for later analysis. A Unity application may also be implemented to provide this visualization in 3D, as shown in FIG. 2.

Testing Results

Using two sensors 102 and a smartphone (e.g., computing device 104), joint angle and muscle activation were recorded in a home environment with two tests. In the first test, a sensor 102 was placed on the bicep and a second on the anterior forearm. The elbow was flexed and extended elbow several times while facing forward, then repeated this after turning 90 degrees clockwise (FIG. 5). Finally, after turning back 90 degrees counterclockwise, several more curls were performed while holding weight.

As described herein, the elbow angle was measured as rotation around the inferred elbow axis (Equation 11). The rotational velocity around this axis, measured by transforming the gyroscope via Equation 12, is also much easier to interpret than the raw recordings in the sensor frame. There appears to be a brief rotation in the first second without corresponding change in the elbow angle, but upon further inspection, this corresponds to a change in both the arm and forearm segments. The rotation of the arm sensor 102 around the elbow axis showed an identical brief change at this time before remaining nearly zero (data not plotted). Finally, the biceps show clear cyclic activation corresponding to the curls, with much greater magnitude after picking up the increasing load.

Figure 8:
FIG. 8 is a photograph that depicts a demonstration of sensor tracking walking with combined monitoring of femur and tibial angle with knee angle and muscle activation from the quadriceps and tibialis anterior.
Figure 9:
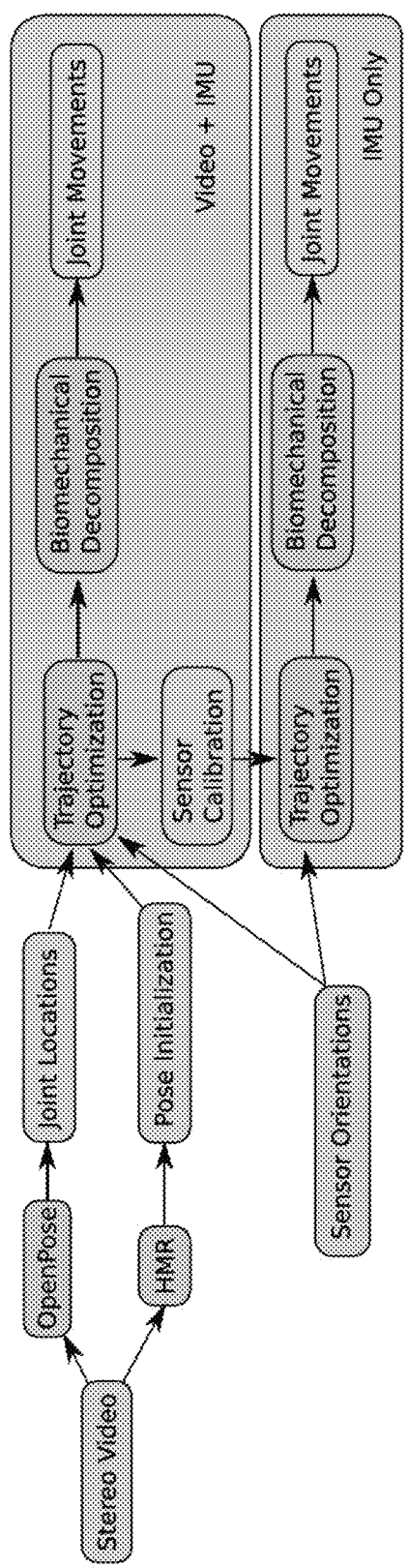
FIG. 9 is a simplified block diagram illustrating an overview of one particular algorithm to combine video data with wearable sensor data for a combined estimate of joint movements. The fusion also produces calibration information allowing subsequent tracking with sensors alone.

In the second test, one sensor 102 was placed on the quadriceps and another over the tibia, allowing knee angle and extensor muscle monitoring. A few steps were taken, followed by several squats and finally several straight leg raises (FIG. 8). Because this occurred without turning, a rotation axis for the thigh and leg could be estimated as their primary axis. This assumption could be removed with an additional sensor 102 tracking the torso. The estimated angles were consistent with the movements described. The quadriceps activity was consistent with the described movements, being cyclically active during walking and squatting but much less when raising the leg with knee extended.

Video Pose Estimation

Stereo Video and Calibration

For more complex movements such as shoulder or hip movement (i.e. multiple axes of rotation), it can be beneficial to use video analysis to detect sensor 102 alignment relative to the body. The video analysis can be used for calibration of sensor 102 alignment relative to the body for improved accuracy. It should be understood that the present embodiment of an algorithm is just one possible embodiment for performing the subject functionality. The application of fusing the data generated from the sensors 102 and then using the information extracted for rehabilitation can be applied to other algorithms and embodiments thereof.

Referring to FIGS. 9 and 11-16, two cameras 210 were mounted pointing in parallel and separated horizontally by approximately 50 cm. It should be noted that two cameras 210 were used for accuracy, however in some embodiments a singular camera 210 such as one included on a smartphone or other mobile device can suffice. Stereo video was acquired with a custom python tool using OpenCV, which allowed recording stereo video from standard USB webcams (Logitech C920 recording at 640×480) that while not hardware synchronized, was sufficiently synchronized for this application. Calibration video was acquired of a checkerboard pattern that could be seen by both cameras and was used to estimate both the intrinsic $\mathcal{M}$, and extrinsic camera parameters with relative rotation $\mathcal{R}$ and offset o (which is zero for the first camera). This parameterizes a simple pinhole camera model that predicts how coordinates in 3D space map onto 2D image space (no distortion parameters are used), which using homogeneous coordinates is written as:

$$\begin{bmatrix} u \\ v \\ 1 \end{bmatrix} = \mathcal{M}[\mathcal{R} \mid o] \begin{bmatrix} x \\ y \\ z \\ 1 \end{bmatrix} \quad (1)$$

Joint Localization and Initial Pose Estimation

Stereo video was analyzed using OpenPose to localize joint keypoints from both cameras. Despite the stereo perspective, it was found that fitting a simple kinematic skeletal model initialized from a neutral pose to be ill-posed, resulting in severely unrealistic poses and temporal discontinuities that could not be smoothed due to local minima. Parameterizing the rotations with quaternions lessened local minima but did not prevent unrealistic postures.

This improved with a more realistic model of the human body. A widely used parameterization of this is the SMPL model shown in FIG. 10, which describes a human-like mesh parameterized by a shape $\beta \in \mathbb{R}^{10}$ and a pose $\theta \in \mathbb{R}^{3 \times K}$, which is 24 rotation vectors (23 joints and a base rotation). This parameterization has more degrees of freedom than the human body and can still generate many implausible poses and it was found that directly optimizing this suffered similar issues.

The local minima of unrealistic postures was avoided by generating initial pose and body shape estimates, $\{\overline{\theta}_t, \overline{\beta}_t\}$, by passing video from one camera through HMR, which regresses from images directly to SMPL parameters. It produces realistic postures due to an adversarial prior used during training.

Optimization for a Temporally Smooth Pose

The prior step takes a stereo video and produces a sequence of stereo keypoints locations with associated confidences: $(x_{tji} \in \mathbb{R}^2, c_{tji})$ and SMPL parameters $(\overline{\theta}_t, \overline{\beta}_t)$ for each time step t, joint j, and camera view i. This first pass estimate has a few limitations: 1) it can allow the body shape to change through time, which should not occur for a single individual, 2) it does not utilize the stereo perspective when generating pose parameters, and indeed the forward pass of HMR may not produce the pose that maximally aligns with the keypoints, 3) crucially the SMPL model parameterizes each joint with three degrees of freedom, which makes decomposing changes in pose into biomechanical movements challenging. The adversarial prior used in HMR results in natural appearing poses, but does not fully enforce known biomechanical constraints.

These limitations are addressed by combining several previously described approaches and solving for a single body shape $\beta$, scale s, pose sequence $\theta_t$ as well as a three-dimensional location $p \in \mathbb{R}^3$ to optimize the following combined losses.

Reprojection Loss

While HMR initialization produces reasonable poses, it still shows misalignment in the more detailed positioning of the joints. This can be improved by optimizing the pose (as opposed to regressing from images to pose) to minimize the error when the pose is reprojected back into image space. Let the 3D location of joints from the SMPL model be defined as $J(\theta, \beta) \in \mathbb{R}^{3 \times P}$. The predicted location of the joint keypoints, $\hat{x}$, can then be computed by scaling the joint positions by s, shifting to position $P_t$ and finally projecting through the camera model, $\mathcal{M}_i \mathcal{R}_i$, learned during setup calibration. Using homogeneous coordinates, this can be written as:

$$\begin{bmatrix} \hat{x}_{i,j,t}(\theta, \beta, s, p) \\ 1 \end{bmatrix} = \mathcal{M}_i[\mathcal{R}_i \mid o_i] \begin{bmatrix} p_t + s J_j(\theta_t, \beta) \\ 1 \end{bmatrix} \quad (2)$$

The reprojection error from the SMPL model to the observed keypoints is weighted by the confidences estimated by OpenPose and then summed over the cameras, joints and time to compute a keypoint loss:

$$\mathcal{L}_{kp}(\theta, \beta, s, p) = \sum_{i,j,t} c_{i,j,t} g(x_{i,j,t} - \hat{x}_{i,j,t}(\cdot)) \quad (3)$$

Where g sums the Huber loss for both the x and y coordinates of the keypoints. The confidences $c_{i,j,t}$ are estimated by OpenPose.

Smoothness Loss

Optimizing with only this projection loss resulted in trajectories containing high frequency noise that tracked noise from the keypoint estimation. This was reduced using a regularizer to encourage a smooth pose trajectory by adding an $L_2$ loss on the change in trajectory. This loss is applied directly to the pose parameters, rather than temporal changes in the 2D and 3D joint positions. Additionally, because some joints were not constrained by the 2D keypoints, a very weak $L_2$ norm was also applied to the pose itself to prevent unnatural appearing changes such as bent feet or twisted ankles. A recent update to OpenPose improves the tracking of hands and foots, which could make this second component unnecessary in the future.

$$\mathcal{L}_{smooth}(\theta) = \lambda_1 \sum_{t=1}^{T} \|\theta_t - \theta_{t-1}\|_2 + \lambda_2 \sum_{t} \|\theta_t\|_2 \quad (4)$$

Kinematic Constraints

While the smoothed pose with these constraints was a good fit to the data, it did not allow a direct mapping to joint angles due to excess degrees of freedom and the ability of joint angles to exceed biomechanical limits. This was solved with an additional regularizer that penalized hinge joints such as the elbow and knee for hyperextension as well as rotation orthogonal to the joint axis.

$$\mathcal{L}_{anatomic}(\theta) = \lambda_3 \left( \sum_{t,l \in h} f(s_l \cdot \theta_{t,l}) + \sum_{t,l \in \perp h} \theta_{t,l}^2 \right) \quad (5)$$

Where h is the set of indices into θ corresponding to valid rotation for hinge joints, $s_t$ indicates the sign of invalid movements, and ⊥h is the set of indices for orthogonal rotation around that joint. The function f(x)=max(x, 0) penalizes joints only for movement in the invalid direction (e.g. hyperextension of the knee or elbow). The hyperparameters were set to $\lambda_1$=1e-2, $\lambda_2$=1e-5, and $\lambda_3$=1e4.

Fitting

The final loss function to optimize the temporally-smooth, biomechanically constrained, stereo informed pose for video alone is:

$$\mathcal{L}_{video}(\theta,\beta,s,p) = \mathcal{L}_{kp}(\theta,\beta,s,p) + \mathcal{L}_{smooth}(\theta) + \mathcal{L}_{anatomic}(\theta) \quad (6)$$

All four parameters were optimized with gradient decent over the entire sequence using TensorFlow 2.0 and Adam optimizing using learning rate decay with an initial rate of 1e-1 decaying to 1e-4. The initial parameters were set to $$\theta_t = \tilde{\theta}_t, \beta = \frac{1}{T}\Sigma\tilde{\beta}_t$$

and s=1 m, and $p_t$ was set to the triangulated location of the mid-hip location.

Video Assisted IMU Calibration

A significant barrier to using IMUs for kinematic tracking is calibrating the orientation of the sensor 102 relative to the body segment on which it is placed. This is required to relate a change in sensor orientation to a change in body segment orientation. In addition, the zero position for the sensor 102 (horizontal facing north) may not align with the zero orientation of the stereo imaging. As discussed above, video analysis can be combined with the data from the sensors 102 to improve accuracy of kinematic tracking by the sensors. By including these offsets as learnable parameters and including the orientation error between body segment and sensor orientation in the loss function, it is possible to calibrate these offsets. The orientation of a body segment in the world reference frame based on the IMU measurement alone can be written as:

$$\hat{R}_g^{b_k}(t) = R_g^k R_k^{k'}(t) R_{k'}^{b_k} \quad (7)$$

Where $R_g^k$ is the rotation from the video global frame to the IMU zero frame k (close to horizontal facing north), $R_k^{k'}(t)$ is the IMU attitude estimate from k to the current frame k', and $R_{k'}^{b_k}$ is the rotation from the IMU to the body segment $b_k$.

A loss term can then be defined between the IMU-based body segment orientation and estimate from the SMPL model, $R_g^{b_k}(\theta_t)$:

$$\mathcal{L}_{IMU}(\theta, \{R_0^k, R_{k'}^{b_k}\}_{k \in K}) = \sum_{t,k \in K} \frac{\arccos Tr\left[ R_g^{b_k}(\theta_t) \hat{R}_g^{b_k}(t)^{-1} \right] - 1}{2} \quad (8)$$

Where K is the set of body segments with sensors on them. The combined loss function used for sessions with video and IMU data that jointly solves for smooth pose trajectory as well as the alignment of the sensors on the body is:

$$\mathcal{L}_{combined} = \mathcal{L}_{IMU}(\theta, \{R_g^k, R_{k'}^{b_k}\}_{k \in K}) + \mathcal{L}_{video}(\theta,\beta,s,p) \quad (9)$$

IMU Only Pose Estimation:

Using these calibration parameters, it is then possible to find a pose trajectory based on IMU data alone by optimizing:

$$\mathcal{L}_{IMU pose} = \mathcal{L}_{IMU}(\theta) + \mathcal{L}_{smooth}(\theta) + \mathcal{L}_{anatomic}(\theta) \quad (10)$$

With sparse sensors, such as monitoring only one limb, this problem is fairly ill-posed as there are many poses that can be consistent with the measurement. Because of this, only the pose parameters being spanned by the sensors were optimized ($\theta_K$).

Pose Parameters to Kinematic Movements

While the SMPL model has proven an incredibly powerful tool for human modeling, the 72 parameters that describe a pose are quite distinct from the smaller set of terms clinicians use such as shoulder abduction or flexion, elbow flexion, and forearm supination. This is not a problem if one is only looking at endpoint location over time, but this is rarely the pertinent measure. Focusing on the arm, the many degrees of freedom in the SMPL model mean that without constraints such as $\mathcal{L}_{anatomic}$, concepts such as flexion of the elbow remaining in a fixed plane relative to the humerus are not preserved. While this constraint does disambiguate elbow flexion and wrist pronation, it does not result in a simple 1:1 mapping for shoulder movements. Shoulder interpretation is challenged by the fact that 1) two linkages relate humerus movement relative to the sternum, 2) the zero-position is not at anatomic neutral, 3) the rotation representation does not match the recommendation from the International Standard of Biomechanics (ISB).

Movements of the shoulder complex are captured in the SMPL model by two linkages that are roughly analogous to the acromioclavicular joint and the glenohumeral joint. While distinguishing these separate biomechanical movements is be important, new datasets that track scapular motion would be needed to validate this is an accurate decomposition. Thus, to describe the humerus position relative to the sternum these two linkage rotations must be multiplied Another issue is the SMPL model origin is a T-pose commonly used in character modeling, compared to the anatomic neutral defined with arms by side and palms facing forward. If $\theta_A$ is the SMPL pose for anatomic neutral and $R(\theta)$ is the rotation of a joint relative to the SMPL neutral, the rotation of the humerus can be computed relative to the clavicle in anatomic terms, $A(\theta)$ as:

$$R_c^h(\theta) = R_{clavicle}^{shoulder}(\theta) R_{shoulder}^{humerus}(\theta) \quad (11)$$

$$A_c^h(\theta) = R_c^h(\theta) R_c^h(\theta_A)^{-1} \quad (12)$$

Figures 10A, 10B:
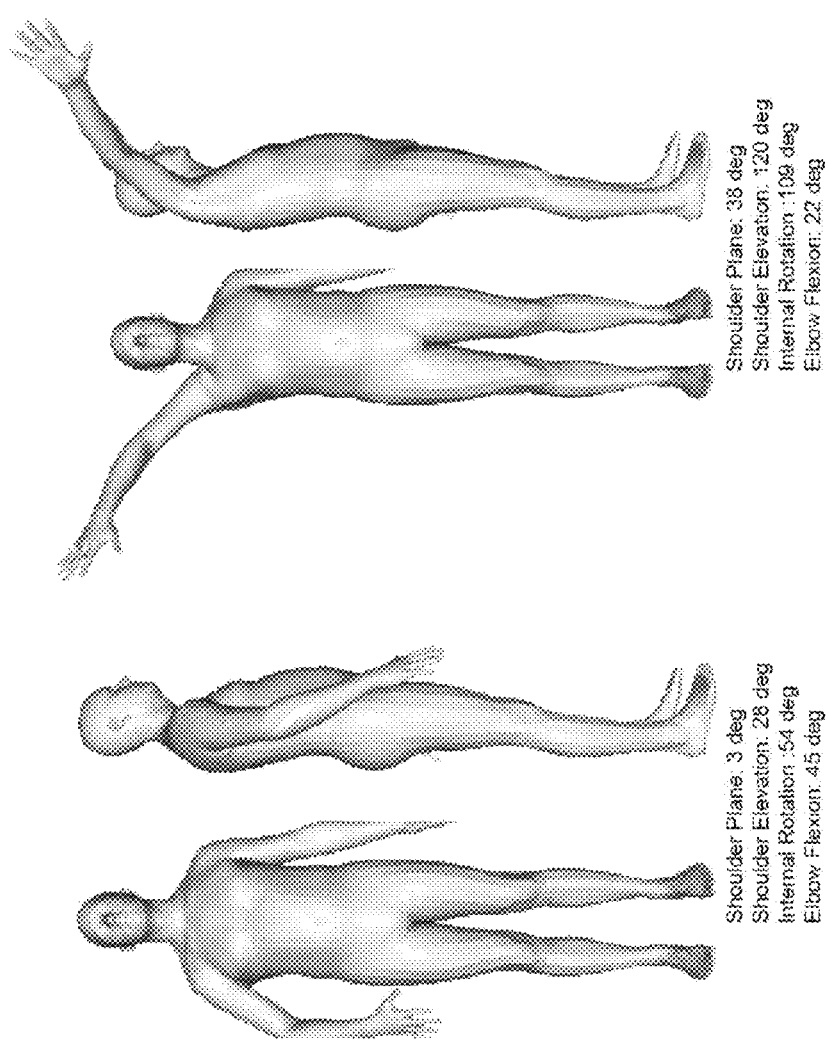
FIGS. 10A and 10B are anatomical diagrams showing example arm positions decomposed into International Society of Biomechanics joint angles.

Finally, this rotation matrix can be decomposed into the movements recommend by the ISB which are three intrinsic Euler rotations—first around the axis of the humerus to define the plane of elevation, then rotating the humerus within that plane, then finally rotating the humerus along the long axis for internal rotation (FIG. 10). When the plane of elevation is forward, this corresponds to flexion and when it is lateral it corresponds to abduction.

Code and Pipeline

In some embodiments, a computer implementation of the present system 100 includes 1) a Jupyter notebook to perform stereo video acquisition, calibrate the cameras to obtain the intrinsic and extrinsic camera parameters, and extract 2D keypoints from stereo video with OpenPose; 2) a notebook to analyze the stereo video with HMR to obtain the initial pose estimates; and 3) a notebook that that optimizes $\mathcal{L}_{combined}$ and $\mathcal{L}_{IMU\,pose}$ using the SMPL model.

Experimentation

The sensor and markerless pose estimation based calibration procedure was tested on a participant with spinal cord injury using a manual wheelchair. Experiments were performed at Shirley Ryan AbilityLab, an inpatient rehabilitation facility, the participant provided informed consent that was approved by Northwestern University's Institutional Review Board. An IMU was placed over the right forearm and upper arm, as tracking arm usage for people with spinal cord injury can be particularly pertinent but challenging. The magnetometers were recalibrated before each experiment as previously described. The subject was encouraged to face the stereo cameras during calibration to keep all keypoints in view.

Pose Trajectory Estimation and Residual Error

Figure 11:
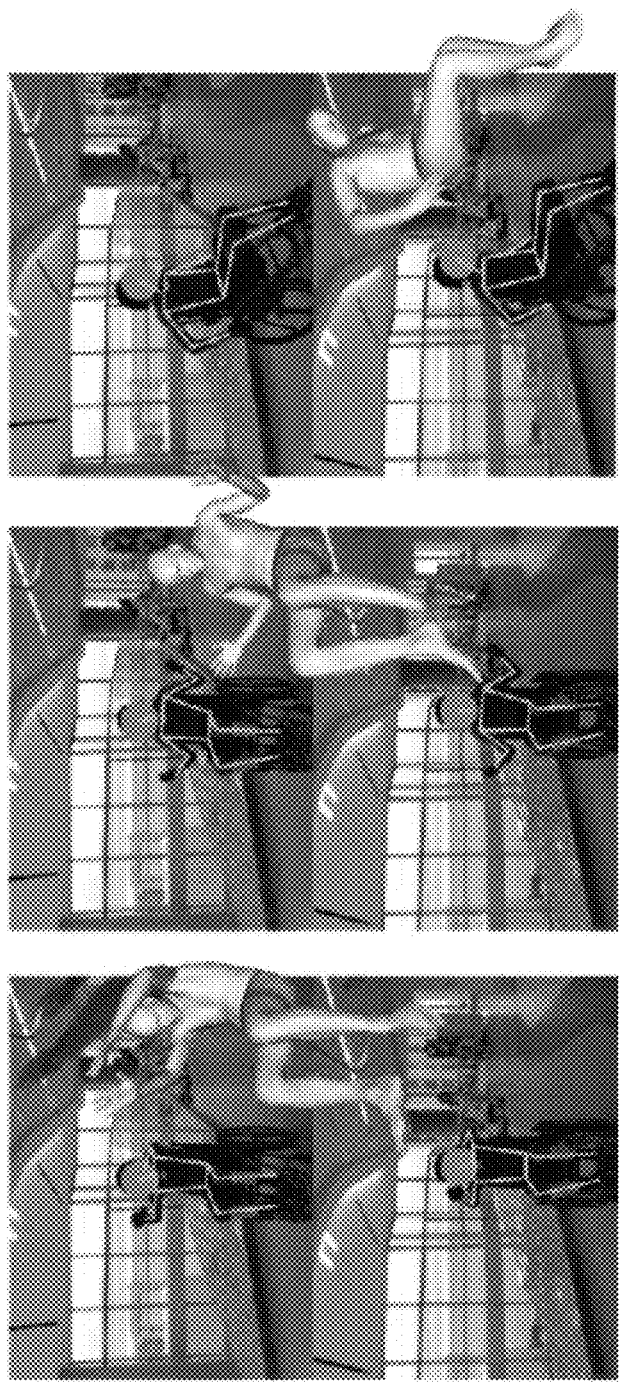
FIG. 11 is a series of photographs showing example reconstructed poses as captured using the dual camera setup.
Figure 12:
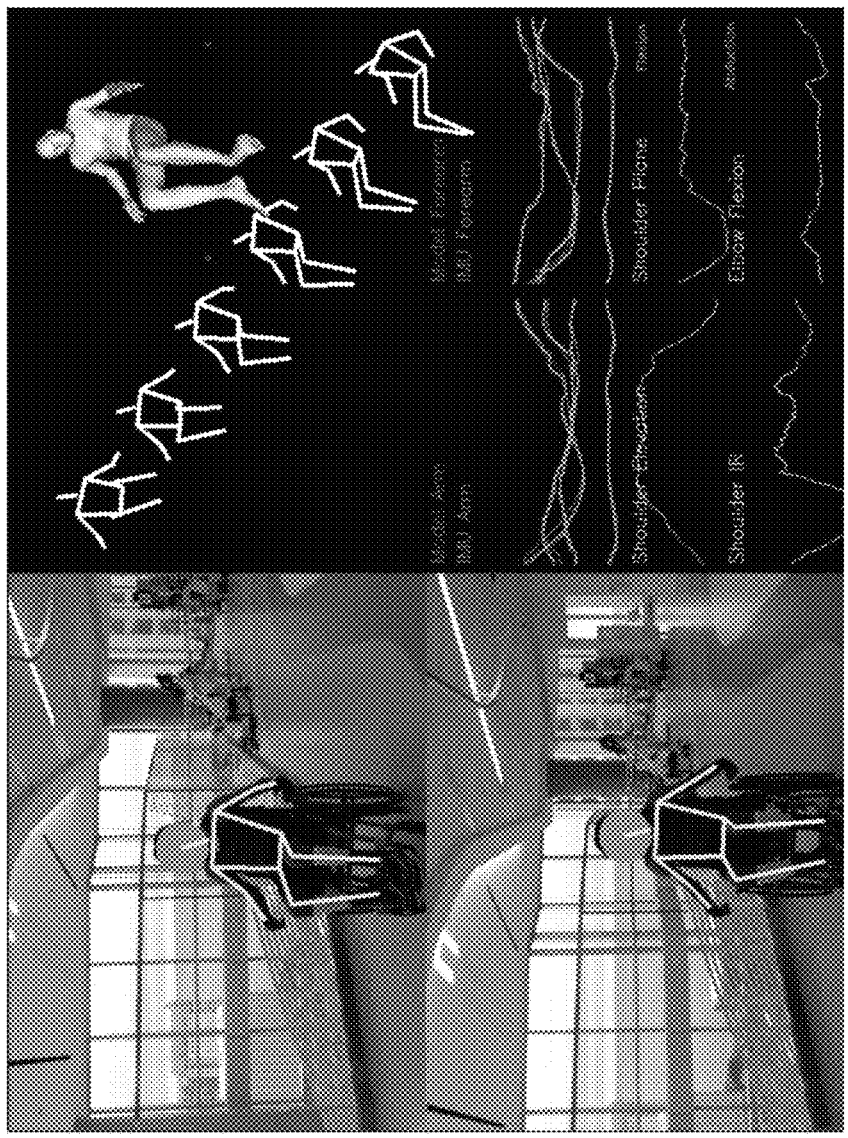
FIG. 12 is a series of images showing demonstration of output from the entire system of FIG. 2.
Figure 13:
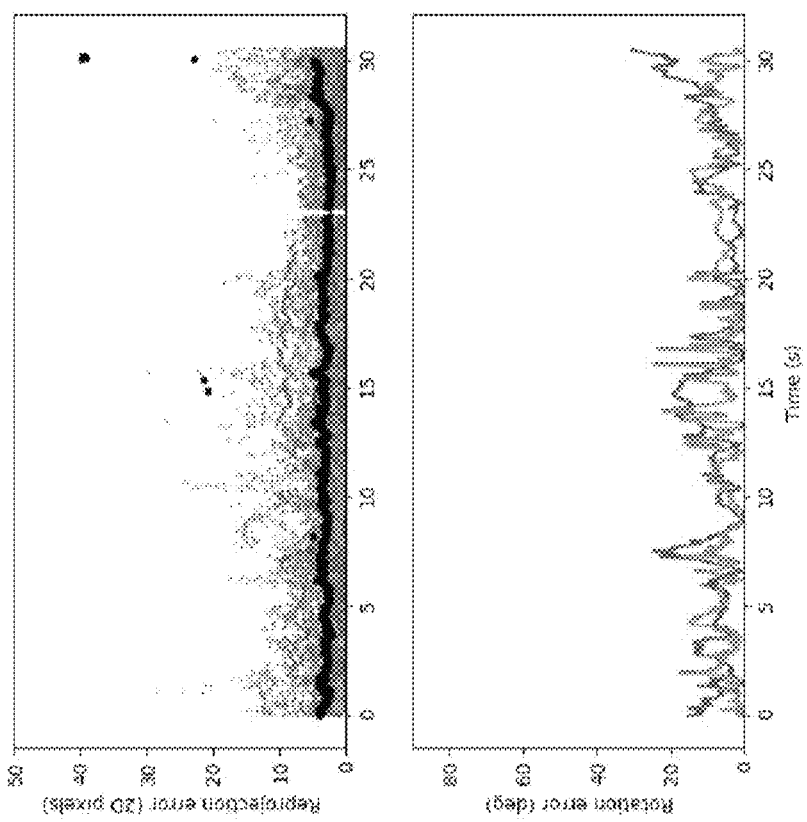
FIG. 13 is a graphical representation showing a Euclidean pixel reprojection error for different joint positions and a graphical representation showing angular reconstruction error from sensors for different sensor angular errors.

Smooth, biomechanically-constrained pose trajectories ($\theta$) with IMU calibrations ($\{R_g^k, R_{k'}^{b_k}\}_{k \in K}$) were obtained by initializing the poses estimates with HMR and the location estimate with the position triangulated from the stereo cameras to the pelvis, and then optimizing $\mathcal{L}_{combined}$ as described above. The quality of fits were assessed both visually and by the 2D keypoint reprojection error and the residual IMU angular error. Example poses reconstructed are shown in FIG. 11 and videos are available at https://youtu.be/zTK4yMQjqsQ. Referring to FIG. 12, a demonstration of output from the entire system 100 is shown. The two video frames on the left show the stereo camera 210 views with the body pose estimated from video and sensor 102 data projected back onto the video. Multiple views of the 3D pose are shown in the upper right panel. The lower right panel shows the orientation of body segments estimated by the combined algorithm and just from the sensor 102 data, showing the agreement from these two. FIG. 12 also shows the joint angles extracted in standard biomechanical conventions.

The video reprojection error was low for both cameras and stable through the experiment, with a median Euclidean reprojection error of 2.3 pixels (FIG. 13), where a 1 cm lateral translation from the average position in 3D space corresponds to a 1.7 pixel shift in image space. This demonstrates with a fixed body shape and scale, it is possible to find a smooth, biomechanically-constrained pose trajectory consistent with the video keypoints. Obtaining this performance depended on a good stereo camera calibration, and particularly ensuring that the corners of the checkerboard were correctly identified in each frame included in the calibration for intrinsic and extrinsic parameters.

In addition, a set of IMU calibration parameters were found resulting in a low residual rotation error between the orientation of the body segmented predicted by the sensors and pose estimate with a median angular error of 6.7° and 5.4° (FIG. 3). The IMU error remained stable through the experiment, demonstrating minimal attitude estimate drift.

Kinematic Decomposition

Figure 14:
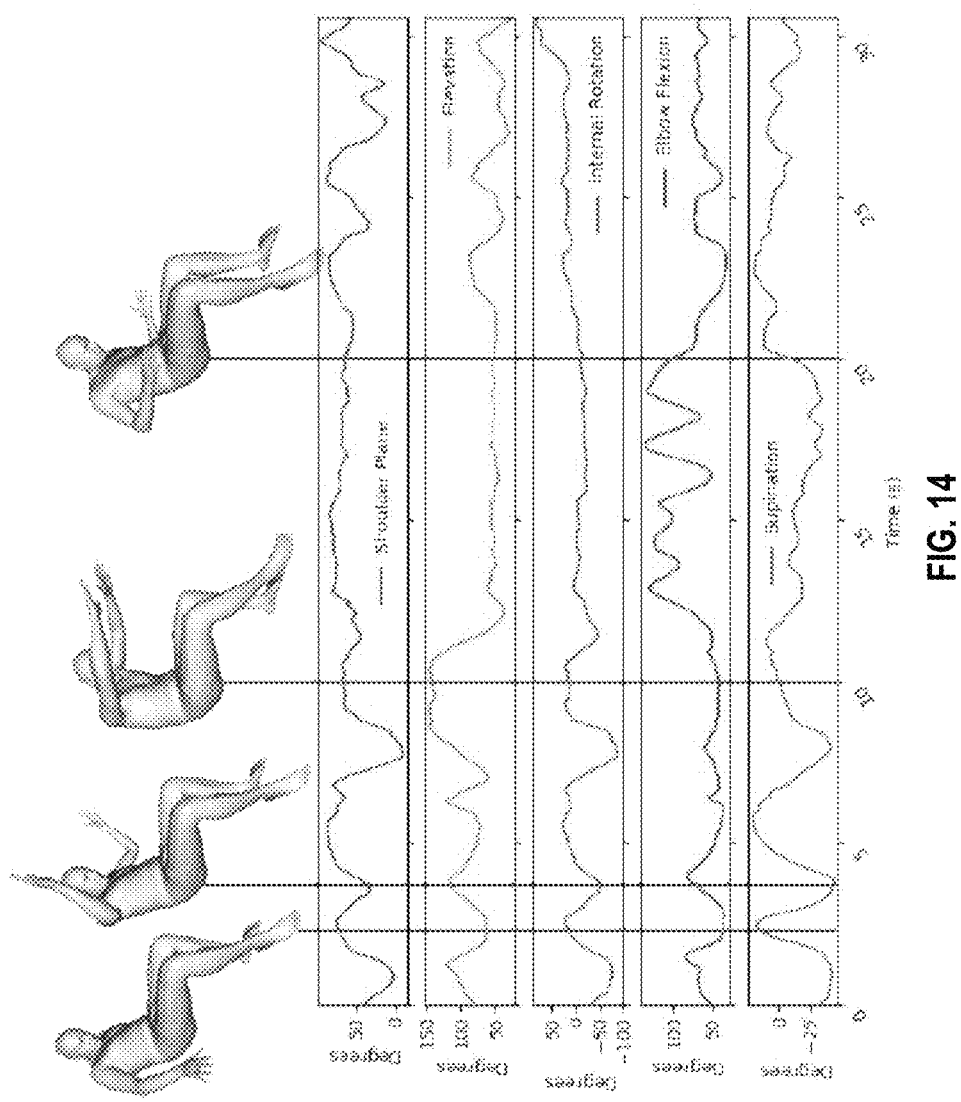
FIG. 14 is a graphical representation showing decomposition of pose trajectory into common kinematic movements with example poses.

The pose trajectory was then decomposed into clinically relevant movements for the right arm including at the shoulder (lateral abduction, forward flexion, and internal/external rotation), flexion at the elbow, and forearm supination and pronation (FIG. 14). Supination cannot be obtained from the 2D keypoints alone (without more detailed hand tracking) and comes from the IMU measurements. This also means only relative changes are meaningful, as the sensor 102 can be placed at an arbitrary location circumferentially around the forearm. The distance along the forearm can also influence the scale of supination/pronation measured as the overlying skin smoothly twists from the elbow orientation to the wrist orientation. Wrist placement would provide the optimal kinematic measurement but does not capture useful EMG data.

Kinematic Decomposition from Calibrated IMU Data

Figure 15:
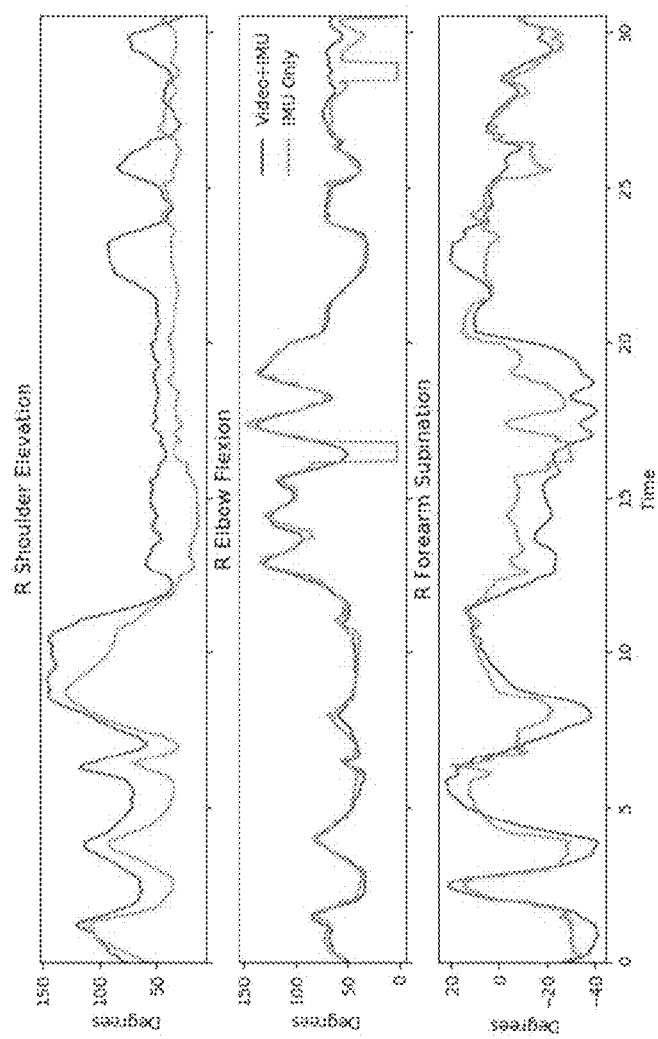
FIG. 15 is a series of graphical representations showing biomechanical movements from the sensors with the camera setup vs the sensors alone.

In many cases in rehabilitation, simultaneous video cannot always be acquired. Using the alignment of the sensor 102 obtained during the calibration phase, it is possible to solve for a subset of the pose parameters that are captured by the sensor 102, $\theta_K$. This can then be decomposed into kinematic measurements. FIG. 15 shows both a comparison between the pose estimated during calibration and then without the video. Tracking the shoulder angle without a sensor 102 on the sternum is slightly ambiguous, so the plane of humerus elevation is confounded with overall body heading.

Figure 16:
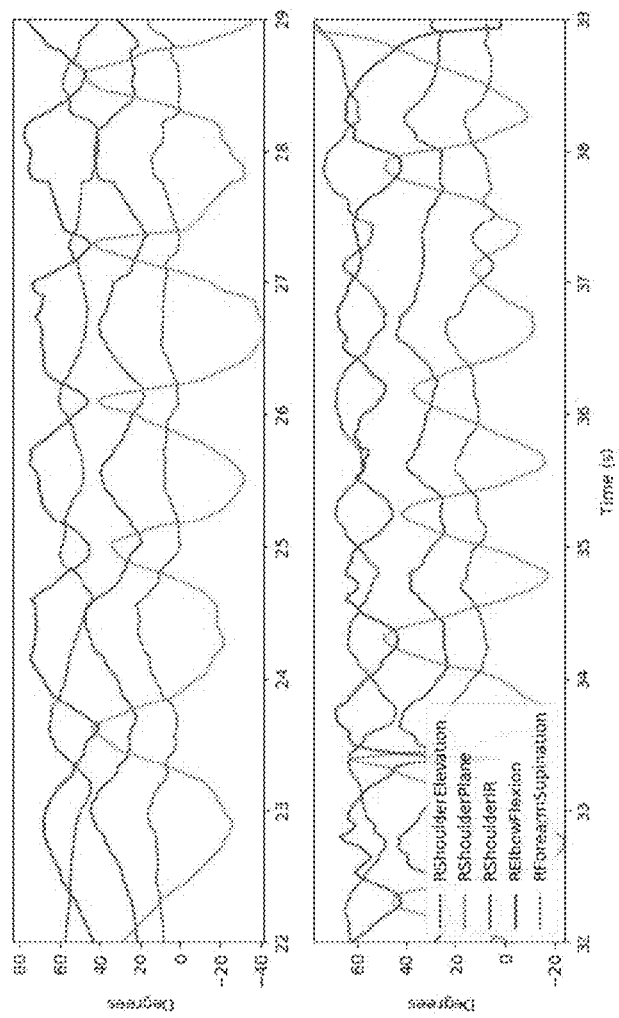
FIG. 16 is a series of graphical representations showing arm movement during wheelchair propulsion computed from sensor data alone over two sessions of pushing.

Despite that, applying the IMU-only pose estimation and kinematic decomposition to data collected during wheelchair propulsion captures the periodic shoulder elevation with elbow flexion as well as the change in elevation plane through the propulsion cycle (FIG. 16).

Game Therapy Application

In some embodiments, the wearable sensor system 100 can be incorporated into therapeutic games or therapy applications that provide biofeedback for building muscle strength and accuracy. Wearable sensors are emerging as a powerful rehabilitation tool that allows muscle activity and movement to be monitored and guided in real time, which makes them particularly suited to translating therapies more broadly into clinical practice. Therapeutic games, sometimes called serious games, are also becoming more common in rehabilitation and have shown promise as a home-based intervention to improve arm function after stroke or SCI. Combined with the wearable sensor system 100, this is a promising approach to create engaging and intrinsically motivating therapies that build on ABTs to dramatically increase both the availability of therapy and the dosing that can be provided. The wearable sensor system 100 records muscle activity and movement with accompanying therapeutic games for the purpose of improving motor recovery after SCI.

Figure 17:
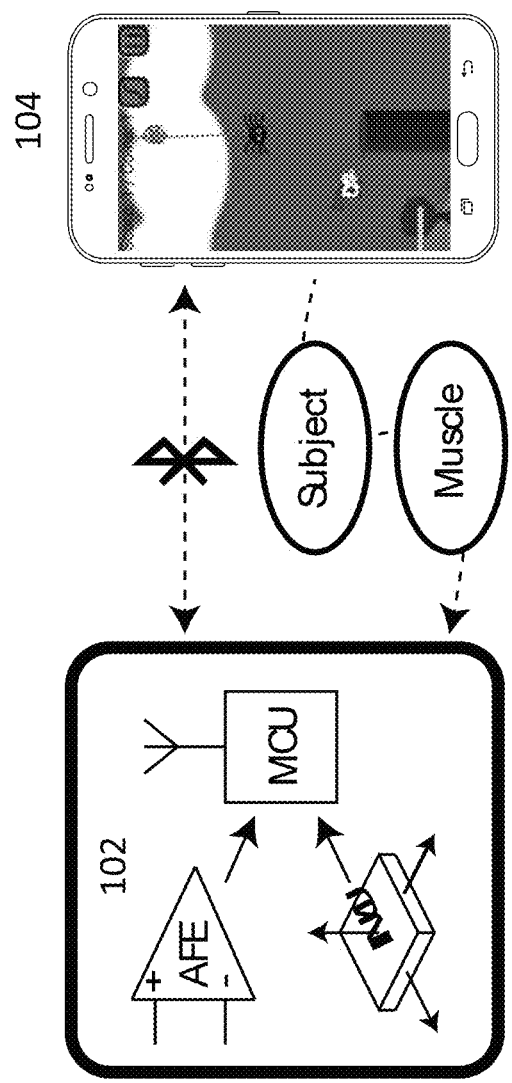
FIG. 17 is a diagram showing a framework of biofeedback loop for use with a therapy game utilizing the system of FIG. 1.
Figure 18:
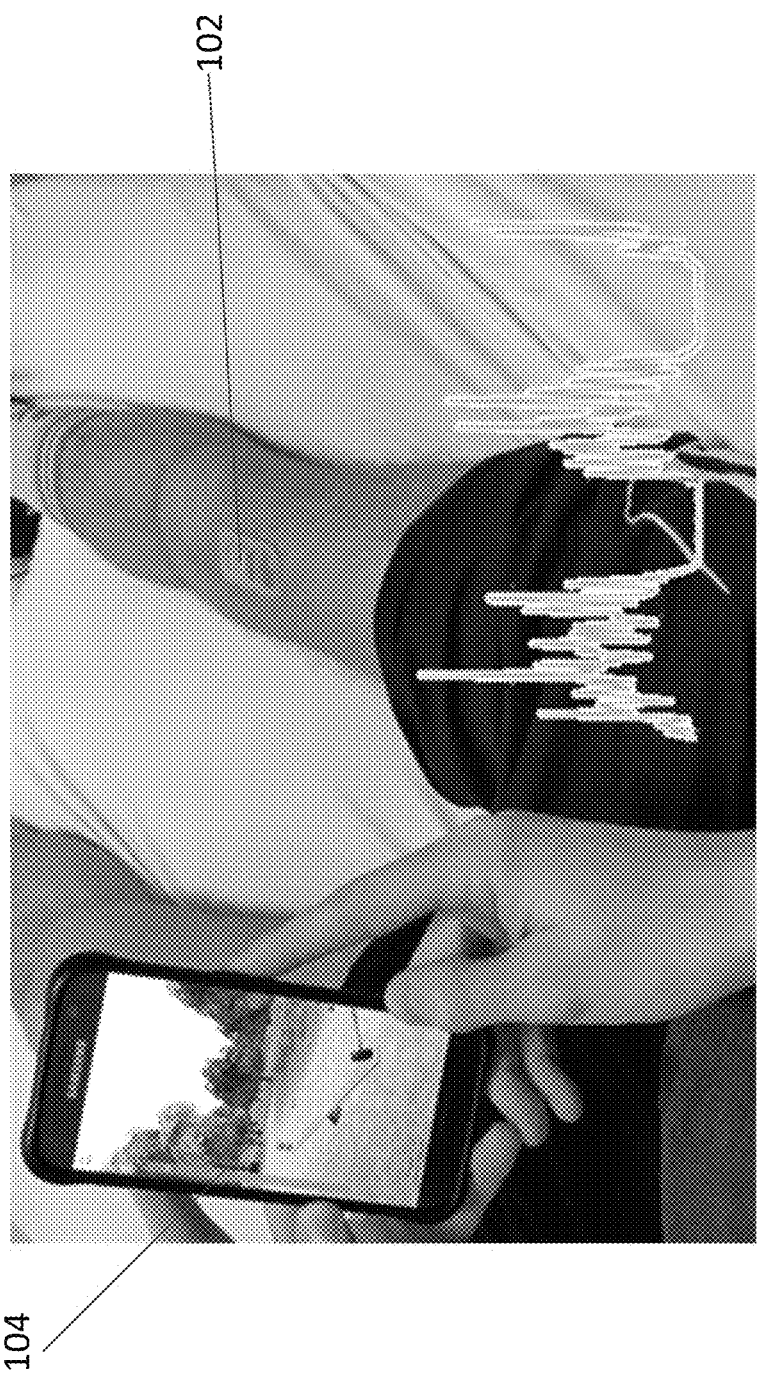
FIG. 18 is a photograph showing a participant with incomplete paraplegia playing the therapy game utilizing the system of FIG. 1.
Figure 19:
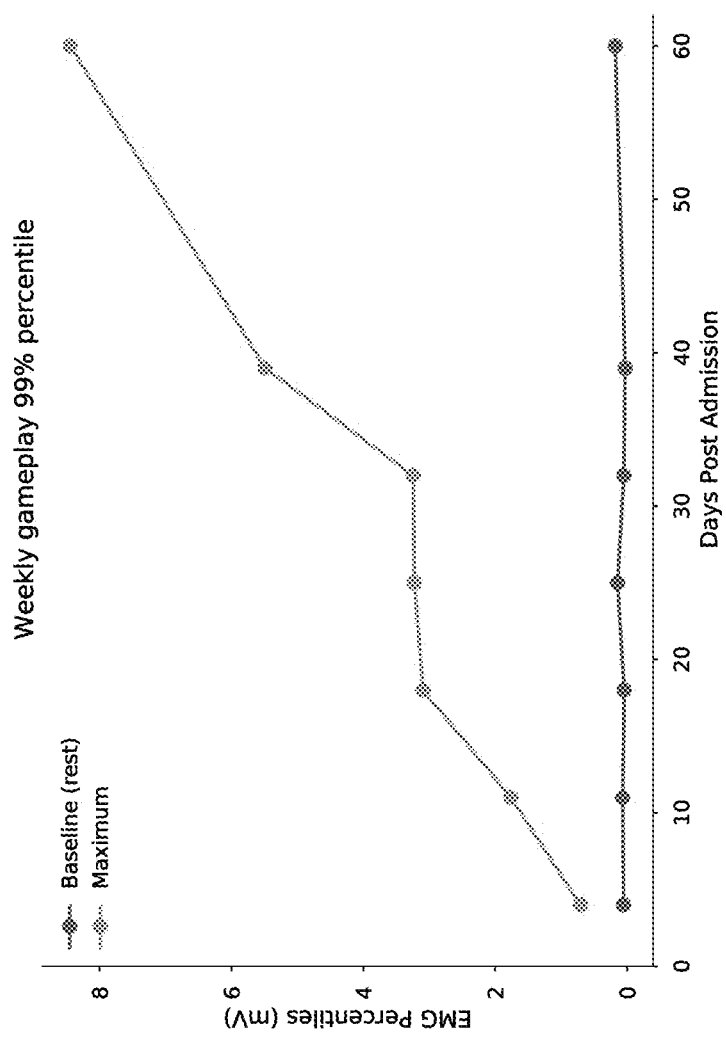
FIG. 19 is a graphical representation showing EMG and muscle activation improvement as a result of playing the therapy game utilizing the system of FIG. 1 for 2 months.

Therapeutic games controlled by the wearable sensor system 100 were implemented in the Unity platform. In one game, cueing the subject to maximally activate a muscle that had a sensor 102 on the overlying skin caused a hammer to propel a ball into the air. This system was tested on a participant with incomplete paraplegia, with the sensor 102 placed over the right vastus medialis. The subject used the system intermittently and ad lib over two months of inpatient rehabilitation. From the time of enrollment, the subject was able to control the game despite initially having only trace activation. The maximal volitional contraction (MVC) was detected during gameplay and showed steady improvements over two months of rehabilitation (FIG. 17-19).

Biofeedback Therapy Application

Spinal cord injury (SCI) affects approximately 18,000 people per year in the US, with incomplete tetraplegia being the most common outcome. People with tetraplegia consistently rank recovery of arm function among their highest priorities in order to improve their independence and quality of life. Activity-based therapies promote motor recovery and are typically most effective with intensive, repetitive practice. Robotic therapy is one approach to facilitate this intensity and volume of practice and can improve arm function, but equipment costs limit wide dissemination and translation to patients. In place of robotics, therapy using visual biofeedback of muscle activity can help people intensely and repetitively activate their muscles, and can also improve strength and function after SCI. To better translate this therapy into practice, the wearable sensor platform 100 for self-dosed biofeedback with therapeutic games using easily deployable and inexpensive technology. Therapeutic games (often called serious games) can be a powerful tool for motor rehabilitation by leveraging principles of motor learning with a therapeutic approach that is intrinsically motivating and engaging. However, there is limited research on the optimal biofeedback protocols for motor recovery after SCI on which to base these therapeutic games, including whether biofeedback can be used to improve motor skill in addition to strength or whether biofeedback based on movement can be more effective than biofeedback based on muscle activity. The following subject matter sets forth some example therapies and possible answers to these questions would enable evidence-based, visually guided biofeedback therapy for motor recovery; which, when delivered with therapeutic games and inexpensive wearable sensors games, would make this therapy more efficacious, engaging and accessible for people with SCI.

Feasibility of using the wearable sensors 102 and therapeutic games for this goal has been established. In some embodiments, feasibility is described as an exemplary proposal training application, with an overall objective being to optimize visually guided biofeedback therapies for recovery of two specific aspects of motor impairments after SCI: weakness and poor motor control. A central hypothesis drives these embodiments, and is based on studies showing the efficacy of electromyographic (EMG) biofeedback therapy for improving strength—is that visually guided biofeedback of EMG and joint movement can improve both strength and motor control. For example, the specific biofeedback protocol used can determine which aspect of the motor impairment will improve the most, as strength and motor skill improvements show task-specificity and correspond to different changes in the nervous system. The rationale is that these optimized and targeted protocols may allow for effective biofeedback-based therapy for motor recovery after SCI and using wearable sensors and therapeutic games may provide broad translation of this treatment to the clinic or home. The central hypothesis of this exemplary training application for implementing the system 100 is tested and two specific aims are considered:

Aim 1: Develop therapy protocols to train motor control accuracy in addition to strength using visual biofeedback of EMG activity from wearable sensors 102. Biofeedback training can improve maximal muscle activation by guiding subjects to repeatedly exceed prior maximal activation levels, but recovering dexterous arm function also requires improving motor skill. Motor accuracy is one important component of motor skill. The present hypothesis is that visually guided EMG biofeedback can also be used to train people with tetraplegia to activate their muscles more accurately. Analogously to strength training, this protocol will have subjects repeatedly produce a cued muscle activation level with progressively increasing accuracy. As therapies after SCI frequently produce task-specific improvements, the protocol for accuracy is expected to result in greater improvement in accuracy than strength, and the protocols for strength to result in the opposite pattern.

Aim 2: Enhance motor control training by using visual biofeedback of joint movements from wearable sensors instead of EMG activity. After SCI, the coordination of agonist and antagonist muscles is often impaired, resulting in reduced movement accuracy and smoothness. Therapy based on the activity of an isolated muscle cannot train this coordination. Preliminary results have shown that the wearable sensor platform 100 can track and provide biofeedback of joint angles and it has been shown that able-bodied people improve their movement accuracy after training with visual biofeedback of movement. The present hypothesis is that visually guided biofeedback of joint movement will improve arm control more than EMG-based biofeedback, as this will provide training of coordinated muscle activity during movements as opposed to isolated muscle activity.

One outcome of the present disclosure is that protocols using visually guided biofeedback of muscle activity and joint angles that specificity target weakness and impaired movement control after SCI, a critical step toward a wearable system for routine self-dosed biofeedback therapy. Combined with therapeutic games that increase intrinsic motivation and participation, the present system 100 is a powerful rehabilitation tool.

Aim 1: Develop Therapy Protocols to Train Motor Control Accuracy in Addition to Strength Using Visual Biofeedback of EMG Activity from Wearable Sensors.

Several groups have shown that training with visual biofeedback of EMG activity can improve volitional activation and even improve functional outcomes such as gait speed and cadence. These studies all used a similar protocol, in which the subject was shown their current EMG activity and a target level that corresponded to their prior maximal volitional contraction (MVC). Subjects were given 20 seconds to try and exceed that target level. When successful, the subsequent target level would increase to this new MVC. These studies reported that subjects were typically fatigued after around 8-10 repetitions. Despite this, a single session improved subjects' MVC, with additional improvements seen in subsequent sessions. Increased amounts of therapy have frequently been shown to confer greater benefits, thus one hypothesis for this aim is that cueing a mixture of submaximal and maximal activations (rather than requiring only MVCs) will reduce fatigue and permit greater therapy volume, ultimately resulting in greater improvements in MVC within a single session.

Figure 20:
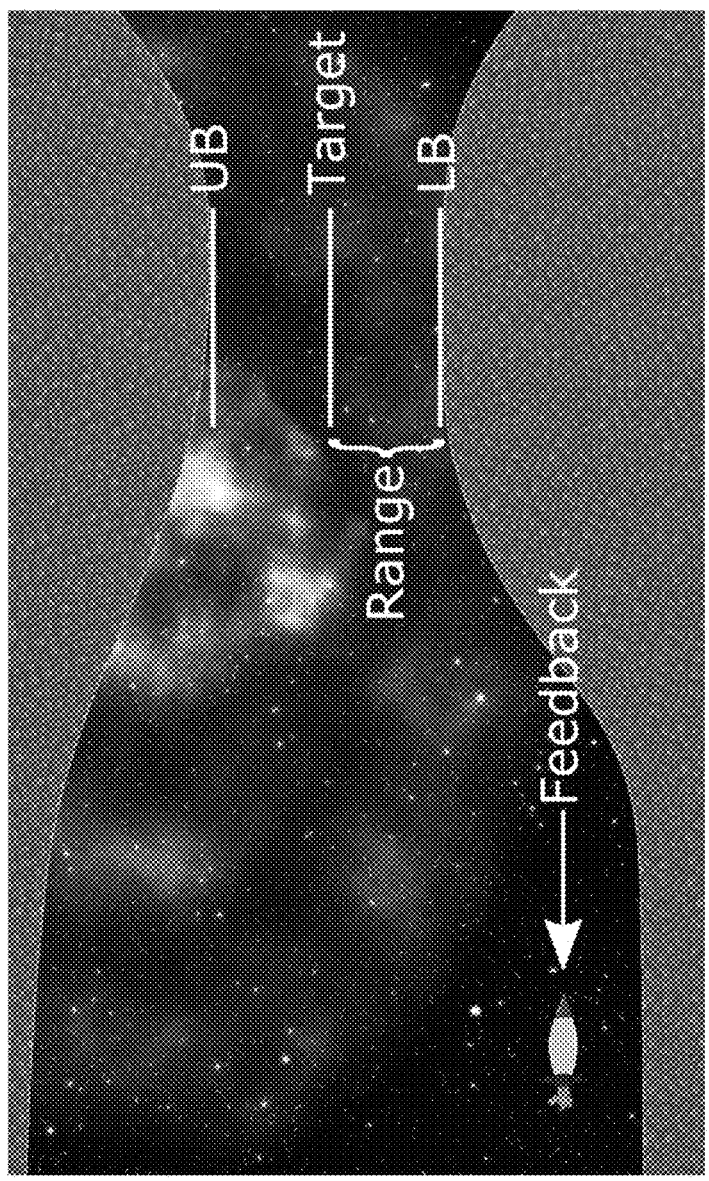
FIG. 20 is a screenshot showing one embodiment of a visual biofeedback game for use with the system of FIG. 1.

Improving strength alone is insufficient for dexterous arm control; people must also improve their motor skill. It is also hypothesized that visually guided EMG biofeedback training could also be used to improve the accuracy of muscle activation. As described in more detail below, accuracy training will use an analogous approach to strength training, but instead of using biofeedback to encourage greater muscle activation, the biofeedback will encourage increasingly accurate activation. Because improvements from therapy are frequently task-specific, these two training strategies are expected to produce specific benefits, i.e., training for accuracy will improve accuracy more than MVC, and strength training will improve MVC more than accuracy. Prior studies did not include a sham biofeedback control, so that is also included. Therapy using visual biofeedback of muscle activity can be provided with the wearable sensor system 100 using a custom therapeutic game. FIG. 20 shows an example game where the feedback controls the vertical location of a spaceship that must navigate varying terrain, as it travels sideways. It should be noted that the game shown is one embodiment of a game which may use the kinematic tracking properties of the system 100, and therapeutic games which utilize the system 100 are not limited to that of FIG. 20. The course is divided into trials during which the height of the course becomes narrower and the user should pass through this gap, which will last 5 seconds. Trials will be successful if the spaceship avoids the boundaries and successful trials will result in positive feedback (e.g., coins and an increasing score).

The dynamics of the game will depend on the specific therapy protocol and include changing how feedback is computed from the muscle activity, the location of the target the to keep the feedback signal near, and the range which defines how narrow the course is.

Game Dynamics Terms:
FB—Visual feedback presented to user.
T—Target activation level.
R—Range around the target that FB should be kept near.

$$UB = T + \frac{R}{2}$$

—Upper bound that FB should stay below.
LB=T-R/2—Lower bound that FB should stay above.
Visual Biofeedback Training for Muscle Control (VBF-C):

For training muscle control, the game will randomize the target location and the feedback (i.e. avatar position) will be directly controlled by the muscle activation: FB=MA. The difficulty will be increased by reducing R, which will bring the upper and lower bounds closer together, thus requiring more accurate muscle control. If the user leaves the target range (i.e. FB>UB or FB<MA) the trial will be unsuccessful and the game will reset for a new trial, but if the user remains in that range for 5 seconds they will get a positive feedback and continue on the course. The game difficultly will adapt to achieve an average performance of 70%, in order to keep the game appropriately challenging but engaging. The target level for each trial will be drawn from a uniform distribution between 10% to 100% of MVC.

Figure 21:
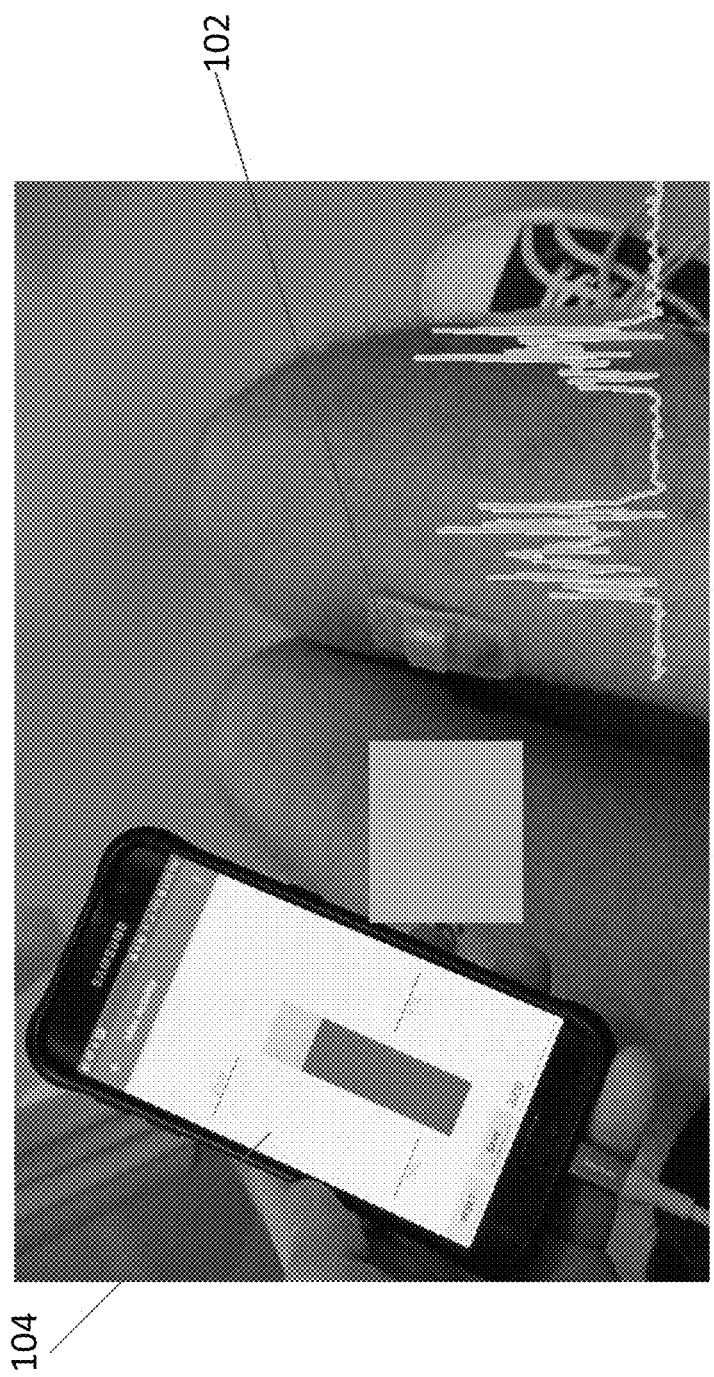
FIG. 21 is a photograph showing measurement of maximal volitional contraction of muscles using the system of FIG. 1, with an overlay trace showing EMG activity.

Visual Biofeedback Training for Muscle Strength (VBF-S):

An exemplary non-limiting implementation of biofeedback controls shall now be described. For training muscle strength, the game will train increasing activation magnitude rather than activation accuracy by altering the feedback signal to prevent the user hitting the ceiling for excessive activity and increasing the difficulty by requiring more activity. More precisely, the feedback signal will track muscle activity until it saturates at the target level, i.e. FB=min(MA,T). This means that passing each trial only requires exceeding the lower bound and there will be no visual feedback for excessive activation. The target for each trial will be drawn from a uniform distribution between 10% MVC to a changing maximum difficulty, with the initial maximum difficulty set to 100% MVC. The maximum difficulty will be adaptively changed for an average performance of 70%, thus as the user achieves more high amplitude activations, the maximum difficulty will increase although easier trials will continue to be included to keep the task engaging. The visualization of feedback and target locations will be scaled by the maximum difficulty, so the game appearance remain similar. FIG. 21 shows measurement of MVC using the wearable sensors 102. The overlay trace in the photograph shows EMG activity recorded by the wearable sensor 102.

Traditional training: In some embodiments, the same game described above can be used with the system 100, but with the protocol used in prior studies, i.e., continuing to increase the target, T. The feedback will be muscle activation (FB=MA). On each trial the user has 20 seconds to exceed the prior maximum activation (the upper bound will not be visualized). Once they are unable to exceed this activity level, the session ends. Trials are separated by two minutes. In prior studies, typically 8-10 trials were successful per session.

Sham training: For sham training purposes, quantitative feedback of muscle activation is not used. Whenever the muscle activity exceeds the baseline resting level (B), the avatar is at the target level, i.e.

$$FB = \begin{cases} T, MA \geq B \\ 0, MA < B \end{cases}.$$

This ensures that the user participates in the game for the duration of the session but gets no specific feedback to improve muscle activation or control.

Study design. Participants have four training sessions that follow a four-way crossover design between these biofeedback protocols. Protocols follow a randomized order with each session separated by at least two days, to washout improvement from prior sessions. Training sessions last for 45 minutes. Both MVC and activation accuracy are measured before and after each session. Subjects are told to maximize their score in the game and are not told which form of therapy they are receiving or how the targets, range or biofeedback is computed. The subject's arm is secured to prevent movement while activating muscles.

Prior to the first session, manual muscle testing along with recordings from the sensors 102 are used to identify weak muscles with detectable volitional EMG activity. If appropriate, the triceps are the primary muscle used, but other muscles in the arm may be used. The subsequent sessions use the same sensor placement, which are measured relative to bony landmarks. Sensor placement is not changed during a session.

Subjects are also surveyed on their qualitative experience with the different therapeutic games and their enjoyment of them to allow continued improvement of experience and engagement for subsequent studies.

Outcomes. The two primary outcomes are the change in MVC and change in activation accuracy from pre-training (T1) to post-training (T2). Both are measured with custom software using the wearable sensors in the same position as during training. Outcomes are measured in physical units (microvolts after bandpass filtering and rectification). Visual feedback is provided of the muscle activation, FB=MA.

MVC is measured as the greatest activation out of three attempts of 5 seconds with 30 seconds between attempts (FIG. 4). Improvement is measured as $MVC_\Delta = MVC_{T2} - MVC_{T1}$ Activation accuracy is measured as the error when trying to maintain a steady activation level at a target level for 5 seconds. This is performed at 10% MVC and repeated three times. The average error is computed for all trials. Improvement is measured as the reduction in error: $ACC_\Delta = E_{T1} - E_{T2}$ Other measures: at the beginning of the first session, manual muscle testing is used to measure strength in both arms to compute the ASIA examination upper extremity muscle score. Strength from the muscle being trained is quantified with a dynamometer.

Analysis The change in both MVC and accuracy is computed for each subject with each training protocol. A greater improvement in MVC for the two strength training protocols (VFB-S and traditional) and a greater improvement in accuracy with VFB-C are anticipated, although the improvements are not expected to be perfectly isolated as all involve practice activating muscles (see FIG. 22 for expected pattern).

A subgroup analysis is also performed based on the strength (measured dynamometry testing as well as initial MVC) to determine how baseline impairment interacts with the efficacy of the interventions. Severe weakness are anticipated that can make VFB-C ineffective, as some subjects are unable to generate graded movement, but strength training protocols are expected to work for these subjects.

Dynamics of skill improvements can be informative and have helped reveal different mechanisms underlying learning. The change in difficulty measures is analyzed for both VFB-S and VFB-C, which indicate if performance saturates over the course of training or continues to improve. This better informs training duration for subsequent studies.

Potential problems and alternative strategies. No problems are anticipated for implementing the described therapeutic games using the system 100, and both the primary and secondary outcome measures are routinely used in labs. While it is hoped that the subjects will be masked from the type of biofeedback they are receiving, if pilot subjects are unable to discover how to play the games without being informed, this masking is dropped and the subjects are informed of the specific training rules to follow.

Using a uniform distribution to select the target difficulty may also result in too many challenging trials—both for the control task and the strength task. For the control task, this would be noted with more errors for higher amplitude targets. This problem can be reduced using a Weber's law style task where the target range is wider for larger amplitude targets. For both the control and strength task, it may be found that too frequent large amplitude trials cause excessive fatigue, which could be mitigated by replacing the uniform distribution with a heavier tailed distribution. These protocols are optimized with pilot trials on able-bodied individuals.

The strength training protocols are anticipated to improve MVC and VFB-C to improve motor control over a single 45-minute training session. However, an interim analysis can be performed after the first 6 subjects to verify this trend. If this is not observed, multiple sessions of each protocol is performed to increase effect size.

Finally, changes in the functional outcomes like manual muscle testing, GRASSP or SCIM-III are intentionally not measured as that level of improvement is not anticipated from a single session. These will be measured in subsequent studies with more prolonged use of this therapy. Electrophysiological measures are also used such as motor evoked responses to study the underlying mechanisms for motor recovery and to characterize changes from training protocols.

Aim 2: Enhance Motor Control Training by Using Visual Biofeedback of Joint Movements from Wearable Sensors Instead of EMG Activity.

Rationale: People with spinal cord injuries (SCI) have impaired coordination of agonist and antagonist muscles in addition to weakness and impaired muscle control, resulting in less reliable movements. Robotic training and ABTs improve arm strength and function through movement based therapies. Given the task-specificity of training, it is hypothesized that movement accuracy will improve more with kinematic (joint angle)-biofeedback than with VFB-C, as it more directly targets impaired movement. This can be provided for subjects with sufficient arm movement in a gravity eliminated position (e.g. using a sling), and if effective could reduce barriers to therapy by reducing the need for expensive robotic equipment.

Figure 22:
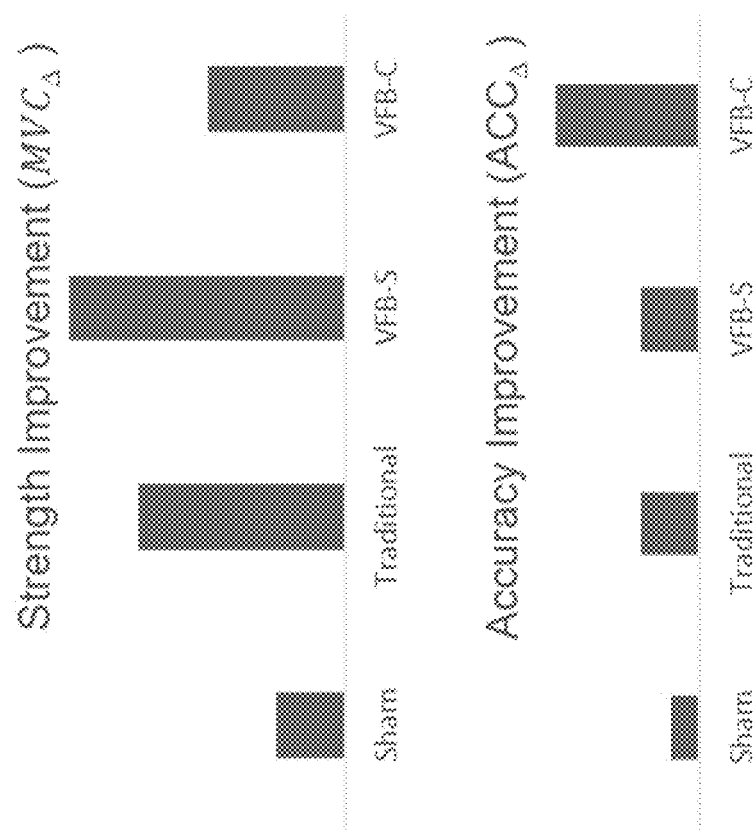
FIG. 22 is a graphical representation showing relative expected improvements in strength (top) and accuracy (bottom) from each therapy protocol.

Preliminary results: Preliminary work towards real-time kinematic tracking includes a complementary filter algorithm that runs on the wearable sensor 102 to fuse the data from the accelerometer, magnetometer, and gyroscope to compute the orientation of an individual sensor 102. Because sensors 102 can be placed on body segments in arbitrary orientations, it is not possible to simply take the orientation difference between two sensors 102 as the joint angle, so an algorithm was developed that infers the joint axis and joint angle from the orientation data of two sensors 102 on either side of the joint. This allows simultaneous measurement of elbow angle and muscle activity in a home environment using only the sensors and a smartphone (FIG. 22).

Methods: The wearable sensors 102 described in Aim 1 will be used, with one placed on the forearm to allow elbow angle tracking and a second placed on the triceps for motion tracking and to detect triceps activation. The VBF-C protocol described in Aim 1 is compared using data from the triceps with movement-based training.

Visual biofeedback movement training (VBF-M) uses the same visualization and dynamics as VBF-C, but the location (e.g. feedback signal) is determined by the elbow angle (i.e. FB=EA). Each trial has a target elbow angle that the user must reach and hold within the set range for 5 seconds. The target elbow angle is drawn randomly between the subject's full flexion and extension. The difficulty is also adapted by adjusting the range around the target angle to keep average performance at 70%, thus encouraging users to hold their position more accurately.

Study design: Subjects for this aim are required to have full elbow extension with their arm placed in a sling to eliminate the effect of gravity. This aim uses a two-arm crossover design with subjects randomized to either VBF-C or VBF-M first with the two sessions separated by several days. Training sessions last for 45 minutes. Secondary outcomes described in Aim 1 are measured prior to the first session.

Movement accuracy: The primary outcome will be improvement in the accuracy of holding a fixed position, analogous to the activation accuracy described in Aim 1. Specifically, users are cued over three trials to hold a target angle (evenly spaced through the subject's range), with visual feedback provided for the elbow angle. The average error is computed over all trials. Improvement is measured as the reduction in angular error: $M_A = E_{T1} - E_{T2}$, measured in degrees.

Analysis: Please see Human Subjects and Clinical Trials Information for full Statistical Plan. Movement accuracy, $M_A$, is anticipated to improve more with VBF-M than VBF-C, Potential problems and alternative strategies: No issues are anticipated for implementing the motion. tracking for biofeedback into therapeutic games The VBF-M protocol requires moving the arm to a location and then holding it there accurately. This is a natural extension of the VBF-C protocol, but may not be as effective as a task that requires continuous movement. A task with healthy people was previously used that required accurately tracking a moving target and shown improvements with this training. In initial pilot studies for this aim on healthy individuals, a static and dynamic version of this task will be compared. The dynamic version will be similar by creating a course with a varying target and would be used for both VBF-C and VBF-M in this aim. If the dynamic task is used, the movement accuracy is also measured with a dynamic target.

Sessions are also run with an additional sensor 102 on the biceps to directly measure the coordination between agonist and antagonist muscles, to see whether this changes in response to training with both VBF-C and VBF-M.

This can be piloted in virtual reality, as this would ensure that participants do not see real joint movements and only see the biofeedback. However, this is not the first line approach, because using VR creates an additional barrier to deployment. As in Aim 1, subjective data is also collected from subjects on the therapeutic games to continue improving them.

CONCLUSION

Monitoring participants at home with wearable sensors is proving increasingly important for rehabilitation, sometimes producing results at odds with traditional laboratory-based outcome measures. This system 100 includes a wearable EMG sensor 102 with an onboard pose (attitude) estimator, smartphone acquisition component, and joint angle-tracking algorithm(s). Using at least the aforementioned components, the system 100 makes it possible to leave the laboratory and continue monitoring joint mechanics and activations in a more natural setting. Once freed from the lab, there are numerous possible applications including tracking biomechanics as people engage in sport or monitoring gait mechanics. This system 100 also has numerous applications in rehabilitation setting, such as objectively quantifying spasticity or tracking recovery of strength after spinal cord injury. Additionally, this can extend prior work providing biofeedback with smartphone games to people with spinal cord injury from EMG-based biofeedback to joint angle-based biofeedback.

Further, an approach for kinematic tracking of rehabilitation patients using inertial sensors optionally fused with video is demonstrated. The video pipeline uses OpenPose and Human Mesh Recovery to compute joint positions and an initial pose estimate for each frame. This is combined with the inertial data to compute a pose trajectory minimizing a loss function that includes the reconstruction error of the inertial and video data as well anatomic and smoothness constraints. This optimization finds the relative orientation of the wearable sensors relative to the body segments, which allows tracking pose trajectories with inertial data alone. Finally, pose parameters for the arm are transformed into clinically interpretable joint angles over time. This approach was tested using standard USB webcams and custom wearable sensors on a person with spinal cord injury to monitor arm movement with wheelchair propulsion even without video data.

Further Applications

The ability to monitor both joint angles and muscle activity at one or multiple joints in real time and provide feedback based on these signals as accommodated by the system 100 has numerous applications in rehabilitation. This could be applied to numerous patient populations but the most obvious would be spinal cord injury, stroke, and general debility, as well as pediatric.

This biofeedback could consist of initially training people to activate their muscles before they are strong enough to actually move the joint, and once they can lift or rotate, the biofeedback can start using the movement instead.

In addition, the feedback could be based on the coordination between movement and muscle activation patterns such as in spinal cord injury monitoring, the evolving coordination in the legs with gait training, or the movement and activation patterns in the arms with wheelchair propulsion. Based on this, more specific feedback could be given to both the patients and the therapy team.

The sensors 102 of the system 100 can allow easy recording of the range of motion. By performing this while monitoring muscle activation, it can be a tool for monitoring spasticity, which is velocity dependent muscle activation. This could be used in a clinic visit to assess spasticity, on follow-up dosing to assess response to therapy (e.g. after chemodenervation (e.g. Botox) or changing oral antispasticity medications or baclofen pump settings). It could also be used in a home setting to allow monitoring of spasticity (both at baseline and in response to therapy).

This biofeedback could be used in monitoring of muscle activity and movement patterns (mentioned above) during therapy. This would be a tool for therapists to better understand what is going on, to track it, and provide more specific feedback. This could be further extended into remote home-rehab or tele-rehab. The system could remotely upload the data and allow the therapist to monitor compliance with home exercise programs and the quality of the movement. It could also provide a computer interface that allows virtual therapy with video conference and the simultaneous streaming of that data to allow therapists to refine their treatments. For example, it could monitor the range of movement in the elbow of a stroke patient performing their home exercise program and additionally quantify the number of repetitions and the amount of spasticity or synergy patterns. Data from all of these could be collected in a database to allow longitudinal monitoring and objective tracking of combined EMG/movement parameters.

Exemplary Computing Device

Figure 23:
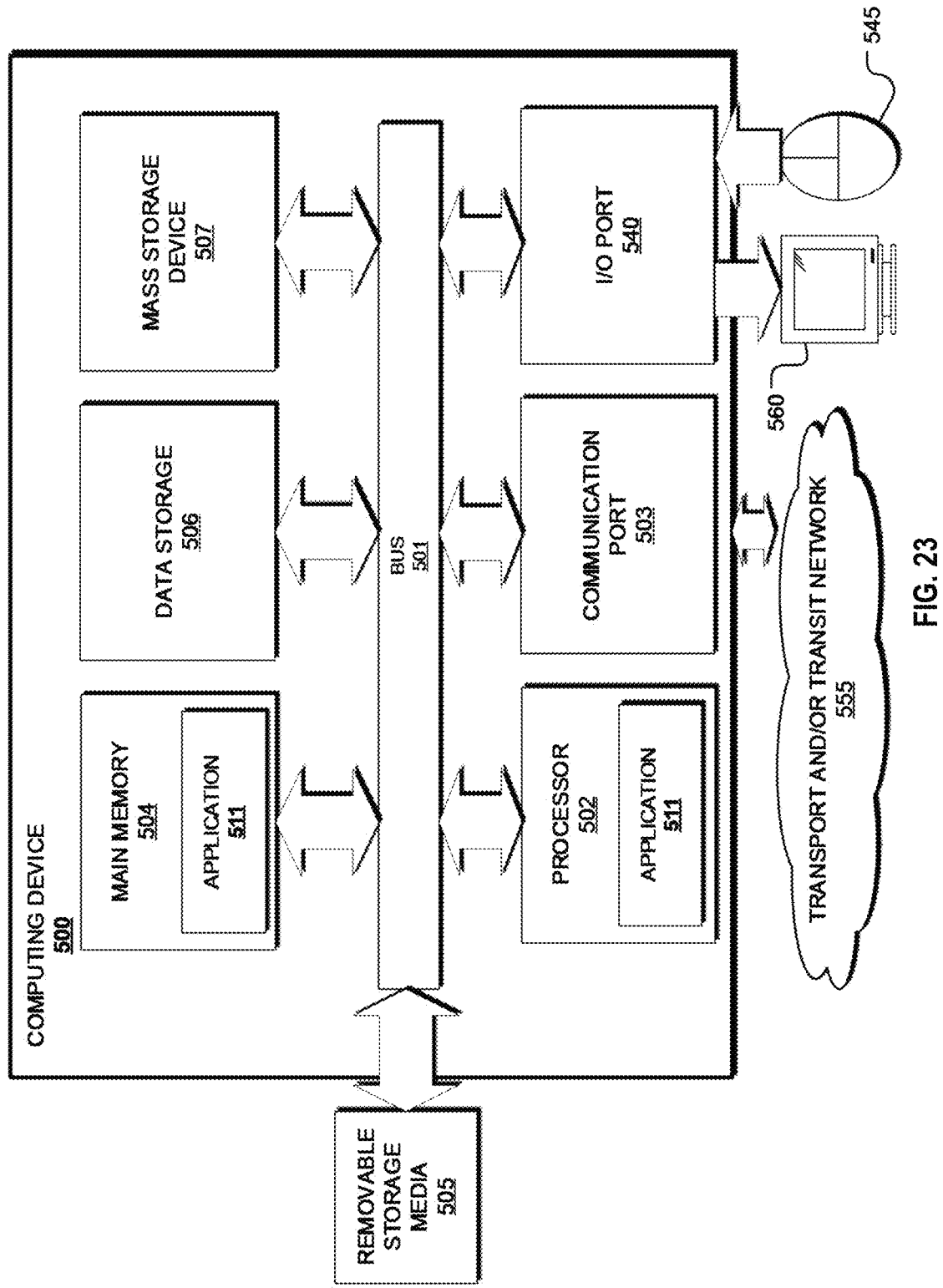
FIG. 23 is a simplified block diagram of a computing device which may be implemented as part of the system described herein.

Referring to FIG. 23, a computing device 500 may be used to implement various aspects of the system 100 described herein. More particularly, in some embodiments, aspects of the system 100 (embodied as an e.g., application 511) may be translated to software or machine-level code, which may be installed to and/or executed by the computing device 500 such that the computing device 500 is configured to interpret/display aspects of the sensor 102 and/or other components of the system 100.

It is contemplated that the computing device 500 is not limited to a sole device and may include any number of devices, such as personal computers, server computers, hand-held or laptop devices, tablet devices, multiprocessor systems, microprocessor-based systems, set top boxes, programmable consumer electronic devices, network PCs, minicomputers, mainframe computers, digital signal processors, state machines, logic circuitries, distributed computing environments, and the like. The device 500 may be one component of a cloud-based environment, for example.

The computing device 500 may include various hardware components, such as a processor 502, a main memory 504 (e.g., a system memory), and a system bus 501 that couples various components of the computing device 500 to the processor 502. The system bus 501 may be any of several types of bus structures including a memory bus or memory controller, a peripheral bus, and a local bus using any of a variety of bus architectures. For example, such architectures may include Industry Standard Architecture (ISA) bus, Micro Channel Architecture (MCA) bus, Enhanced ISA (EISA) bus, Video Electronics Standards Association (VESA) local bus, and Peripheral Component Interconnect (PCI) bus also known as Mezzanine bus.

The computing device 500 may further include a variety of memory devices and computer-readable media 507 that includes removable/non-removable media and volatile/nonvolatile media and/or tangible media, but excludes transitory propagated signals. Computer-readable media 507 may also include computer storage media and communication media. Computer storage media includes removable/non-removable media and volatile/nonvolatile media implemented in any method or technology for storage of information, such as computer-readable instructions, data structures, program modules or other data, such as RAM, ROM, EEPROM, flash memory or other memory technology, CD-ROM, digital versatile disks (DVD) or other optical disk storage, magnetic cassettes, magnetic tape, magnetic disk storage or other magnetic storage devices, or any other medium that may be used to store the desired information/data and which may be accessed by the computing device 500. Communication media includes computer-readable instructions, data structures, program modules, or other data in a modulated data signal such as a carrier wave or other transport mechanism and includes any information delivery media. The term "modulated data signal" means a signal that has one or more of its characteristics set or changed in such a manner as to encode information in the signal. For example, communication media may include wired media such as a wired network or direct-wired connection and wireless media such as acoustic, RF, infrared, and/or other wireless media, or some combination thereof. Computer-readable media may be embodied as a computer program product, such as software stored on computer storage media.

The main memory 504 includes computer storage media in the form of volatile/nonvolatile memory such as read only memory (ROM) and random access memory (RAM). A basic input/output system (BIOS), containing the basic routines that help to transfer information between elements within the computing device 500 (e.g., during start-up) is typically stored in ROM. RAM typically contains data and/or program modules that are immediately accessible to and/or presently being operated on by processor 502. Further, data storage 506 in the form of Read-Only Memory (ROM) or otherwise may store an operating system, application programs, and other program modules and program data.

The data storage 506 may also include other removable/non-removable, volatile/nonvolatile computer storage media. For example, the data storage 506 may be: a hard disk drive that reads from or writes to non-removable, nonvolatile magnetic media; a magnetic disk drive that reads from or writes to a removable, nonvolatile magnetic disk; a solid state drive; and/or an optical disk drive that reads from or writes to a removable, nonvolatile optical disk such as a CD-ROM or other optical media. Other removable/non-removable, volatile/nonvolatile computer storage media may include magnetic tape cassettes, flash memory cards, digital versatile disks, digital video tape, solid state RAM, solid state ROM, and the like. The drives and their associated computer storage media provide storage of computer-readable instructions, data structures, program modules, and other data for the computing device 500.

A user may enter commands and information through a user interface 540 (displayed via a monitor 560) by engaging input devices 545 such as a tablet, electronic digitizer, a microphone, keyboard, and/or pointing device, commonly referred to as mouse, trackball or touch pad. Other input devices 545 may include a joystick, game pad, satellite dish, scanner, or the like. Additionally, voice inputs, gesture inputs (e.g., via hands or fingers), or other natural user input methods may also be used with the appropriate input devices, such as a microphone, camera, tablet, touch pad, glove, or other sensor. These and other input devices 545 are in operative connection to the processor 502 and may be coupled to the system bus 501, but may be connected by other interface and bus structures, such as a parallel port, game port or a universal serial bus (USB). A monitor 560 or other type of display device may also be connected to the system bus 501. The monitor 560 may also be integrated with a touch-screen panel or the like.

The computing device 500 may be implemented in a networked or cloud-computing environment using logical connections of a network interface 503 to one or more remote devices, such as a remote computer. The remote computer may be a personal computer, a server, a router, a network PC, a peer device or other common network node, and typically includes many or all of the elements described above relative to the computing device 500. The logical connection may include one or more local area networks (LAN) and one or more wide area networks (WAN), but may also include other networks. Such networking environments are commonplace in offices, enterprise-wide computer networks, intranets and the Internet.

When used in a networked or cloud-computing environment, the computing device 500 may be connected to a public and/or private network through the network interface 503. In such embodiments, a modem or other means for establishing communications over the network is connected to the system bus 501 via the network interface 503 or other appropriate mechanism. A wireless networking component including an interface and antenna may be coupled through a suitable device such as an access point or peer computer to a network. In a networked environment, program modules depicted relative to the computing device 500, or portions thereof, may be stored in the remote memory storage device.

Certain embodiments are described herein as including one or more modules. Such modules are hardware-implemented, and thus include at least one tangible unit capable of performing certain operations and may be configured or arranged in a certain manner. For example, a hardware-implemented module may comprise dedicated circuitry that is permanently configured (e.g., as a special-purpose processor, such as a field-programmable gate array (FPGA) or an application-specific integrated circuit (ASIC)) to perform certain operations. A hardware-implemented module may also comprise programmable circuitry (e.g., as encompassed within a general-purpose processor or other programmable processor) that is temporarily configured by software or firmware to perform certain operations. In some example embodiments, one or more computer systems (e.g., a stand-alone system, a client and/or server computer system, or a peer-to-peer computer system) or one or more processors may be configured by software (e.g., an application or application portion) as a hardware-implemented module that operates to perform certain operations as described herein.

Accordingly, the term "hardware-implemented module" encompasses a tangible entity, be that an entity that is physically constructed, permanently configured (e.g., hard-wired), or temporarily configured (e.g., programmed) to operate in a certain manner and/or to perform certain operations described herein. Considering embodiments in which hardware-implemented modules are temporarily configured (e.g., programmed), each of the hardware-implemented modules need not be configured or instantiated at any one instance in time. For example, where the hardware-implemented modules comprise a general-purpose processor configured using software, the general-purpose processor may be configured as respective different hardware-implemented modules at different times. Software may accordingly configure the processor 502, for example, to constitute a particular hardware-implemented module at one instance of time and to constitute a different hardware-implemented module at a different instance of time.

Hardware-implemented modules may provide information to, and/or receive information from, other hardware-implemented modules. Accordingly, the described hardware-implemented modules may be regarded as being communicatively coupled. Where multiple of such hardware-implemented modules exist contemporaneously, communications may be achieved through signal transmission (e.g., over appropriate circuits and buses) that connect the hardware-implemented modules. In embodiments in which multiple hardware-implemented modules are configured or instantiated at different times, communications between such hardware-implemented modules may be achieved, for example, through the storage and retrieval of information in memory structures to which the multiple hardware-implemented modules have access. For example, one hardware-implemented module may perform an operation, and may store the output of that operation in a memory device to which it is communicatively coupled. A further hardware-implemented module may then, at a later time, access the memory device to retrieve and process the stored output. Hardware-implemented modules may also initiate communications with input or output devices.

It should be understood from the foregoing that, while particular embodiments have been illustrated and described, various modifications can be made thereto without departing from the spirit and scope of the invention as will be apparent to those skilled in the art. Such changes and modifications are within the scope and teachings of this invention as defined in the claims appended hereto.

What is claimed is:

1. A system for utilizing wearable sensors to record muscle activity and provide biofeedback for rehabilitation with kinematic monitoring, comprising:
 a plurality of sensors configured to be aligned on a limb of a user, each of the plurality of sensors including an inertial measurement unit (IMU) for generating inertial data and a plurality of electromyography (EMG) electrodes for generating muscle EMG data; and
 a processor in operable communication with the plurality of sensors, the processor configured to:
 estimate a pose of the limb of the user, by estimating an attitude of a first sensor and an attitude of a second sensor of the plurality of sensors, estimate a joint angle of the limb, the joint angle measured as a rotation magnitude about an inferred axis of the limb defined by the attitude of the first sensor and the attitude of the second sensor, and
 execute a therapy application, the therapy application configured to utilize the EMG data, and pose and joint angle of the limb as estimated from the plurality of sensors to detect muscle activity and movement related to the limb and provide the biofeedback to the user for rehabilitation.

2. The system of claim 1, wherein the processor, by executing the therapy application, is configured to cue, via a display, an instruction to apply a predetermined movement of the limb or muscle activity of the limb for a predetermined therapy protocol, and provide visual biofeedback related to a response of the user to the instruction as expressed by the muscle activity and movement related to the limb as detected.

3. The system of claim 1, wherein the processor, by executing the therapy application, provides a game to the user with visual interaction associated with the game provided to the user via a display, and the processor tracks changes in the muscle activity and movement related to the limb over a predetermined time period as the user engages the game to pursue a target activation level associated with the game related to muscle control or muscle strength.

4. The system of claim 3, wherein processor, by executing the game as configured, alters visual feedback presented to the user via the display according to an upper bound and a lower bound, and range around the target activation level associated with a given therapy task to provide visual biofeedback therapy.

5. The system of claim 1, wherein each of the plurality of sensors implement firmware that digitizes the muscle EMG data, and applies additional digital bandpass filtering to the muscle EMG data, the muscle EMG data communicated to the processor in parallel with the inertial data to accommodate simultaneous monitoring to changes in the inertial data and the muscle EMG data.

6. The system of claim 1, wherein the processor measures an orientation of a sensor of the plurality of sensors by transforming magnetometer, accelerometer, and gyroscope measurements of the inertial data.

7. The system of claim 6, wherein the processor combines rotation angles from multiple sensors of the plurality of sensors to estimate a plurality of joint angles.

8. A system, comprising:
 a plurality of sensors configured to be aligned on a body part of a user, each of the plurality of sensors including an inertial measurement unit (IMU) for generating inertial data and a plurality of electromyography (EMG) electrodes for generating muscle EMG data; and
 a plurality of video-capable cameras configured for capturing a video of a pose of the user, the video including a plurality of frames; and
 a processor in operable communication with the plurality of sensors and the plurality of video-capable cameras, the processor including instructions that, when executed, cause the processor to:

collect the video from the plurality of video-capable cameras and the inertial data from each of the plurality of sensors:
estimate a pose of a limb of the user, by estimating an attitude of a first sensor and an attitude of a second sensor of the plurality of sensors, estimate a joint angle of the limb, the joint angle and pose accommodating detection of muscle activity and movement related to the limb; and
calibrate an orientation and a position of each of the plurality of sensors relative to a body segment of the user, based on the video.

9. The system of claim 8, further comprising:
wherein the processor is further configured to:
extract joint locations for each joint in each frame of the plurality of frames of the video, wherein to estimate the pose of the user, the processor determines an initial pose estimate for each frame of the plurality of frames of the video;
optimize a pose trajectory to fit the joint locations based on the initial pose estimate from each frame of the plurality of frames of the video and the inertial data from each of the plurality of sensors to determine biomechanical constraints; and
determine the calibration of sensor orientations relative to body segment orientation:
wherein to estimate the joint angle of the limb, the processor determines one or more joint angles for the body parts of the user.

10. The system of claim 9, wherein the steps of extracting joint locations and determining an initial pose estimate for each frame of the plurality of frames produce a sequence of joint keypoints with associated confidences for each timestamp, joint, and camera view of the video.

11. The system of claim 10, wherein the step of optimizing the pose trajectory includes determining a predicted location of each of the joint keypoints by application of one or more smoothing factors and the biomechanical constraints.

12. The system of claim 9, wherein the joint angles are inferred using the biomechanical constraints.

13. The system of claim 9, wherein the joint angles are determined using a relative rotation of each of the plurality of sensors.

14. The system of claim 9, further comprising:
a game framework executable by the processor, the game framework configured to utilize the pose trajectory and one or more joint angles determined using the plurality of sensors to provide biofeedback to the user for rehabilitation.

15. The system of claim 8, wherein the processor is further configured to: execute a therapy application, the therapy application configured to utilize the EMG data, and pose and joint angle of the limb as estimated from the plurality of sensors to detect muscle activity and movement related to the limb and provide biofeedback to the user for rehabilitation.

16. A system, comprising:
a plurality of sensors configured to be aligned along a limb of a user, each of the plurality of sensors including an inertial measurement unit (IMU) for generating inertial data and a plurality of electromyography (EMG) electrodes for generating muscle EMG data, wherein the inertial data includes gyroscope measurements, accelerometer measurements, and magnetometer measurements; and
a processor in operable communication with the plurality of sensors, the processor configured to:
compute a pose estimation of the limb of the user by generating an estimate of an attitude of a first sensor and an estimate of an attitude of a second sensor of the plurality of sensors, wherein
the estimate of the attitude of the first sensor and the estimate of the attitude of the second sensor are generated based on the gyroscope measurements, correcting a drift in the estimate of the attitude of the first sensor and a drift in the estimate of the attitude of the second sensor based on the accelerometer measurements and the magnetometer measurements, and
compute a joint angle estimation of the limb, wherein the joint angle is measured as a rotation magnitude about an inferred axis of the limb defined by the attitude of the first sensor and the attitude of the second sensor,
wherein the joint angle estimation and pose estimation accommodating detection of muscle activity and movement related to the limb.

17. The system of claim 16, further comprising:
a plurality of cameras that capture a video of a pose of the user, the video including a plurality of frames that accommodate modeling of biomechanically plausible pose trajectory.

18. The system of claim 17, wherein the processor includes further instructions that, when executed, cause the processor to:
collect the video from the plurality of cameras and the inertial data from each of the plurality of sensors;
extract joint locations for each joint in each frame of the plurality of frames of the video:
determine an initial pose estimate for each frame of the plurality of frames of the video:
optimize a pose trajectory to fit the joint locations based on the initial pose estimate from each frame of the video and the inertial data from each of the plurality of sensors to determine biomechanical constraints;
determine a calibration of sensor orientations relative to body segment orientations; and
determine one or more joint angles for a body parts of the user.

19. The system of claim 18, further comprising:
a game framework executable by the processor, the game framework configured to utilize the pose trajectory and the one or more joint angles to provide biofeedback to the user for rehabilitation.

* * * * *